(12) United States Patent
Buma et al.

(10) Patent No.: US 8,361,161 B2
(45) Date of Patent: Jan. 29, 2013

(54) KIT AND METHOD FOR FIXATING A PROSTHESIS OR PART THEREOF AND/OR FILLING OSSEOUS DEFECTS

(75) Inventors: Pier Buma, Nijmegen (NL); Berend Willem Schreurs, Malden (NL); Nicolaas Jacobus Joseph Verdonschot, Nijmegen (NL); Lucas Hubert Bernard Walschot, Nijmegen (NL); Thomas Johannes Josephus Hubertus Slooff, Westerbeek (NL); Willem Cornelis Van't Wout, Sr., Zevenhuizen (NL)

(73) Assignee: Fondel Finance B.V., Rotterdam (NL)

( * ) Notice: Subject to any disclaimer, the term of this patent is extended or adjusted under 35 U.S.C. 154(b) by 412 days.

(21) Appl. No.: 12/463,038

(22) Filed: May 8, 2009

(65) Prior Publication Data
US 2009/0306673 A1 Dec. 10, 2009

Related U.S. Application Data

(63) Continuation of application No. PCT/NL2007/050560, filed on Nov. 12, 2007.

(30) Foreign Application Priority Data

Nov. 10, 2006 (NL) .................................. 1032851

(51) Int. Cl.
*A61F 2/32* (2006.01)
(52) U.S. Cl. .................................. 623/22.11
(58) Field of Classification Search ............... 623/22.11, 623/22.33, 23.19, 23.2, 23.26, 23.29, 23.37, 623/23.48, 23.5–23.6, 23.61, 23.62, 23.73, 623/23.74
See application file for complete search history.

(56) References Cited

U.S. PATENT DOCUMENTS

| | | | | |
|---|---|---|---|---|
| 3,855,638 | A | * | 12/1974 | Pilliar ........................ 623/23.55 |
| 4,146,936 | A | * | 4/1979 | Aoyagi et al. ............. 623/23.57 |
| 4,202,055 | A | * | 5/1980 | Reiner et al. ............... 623/23.57 |
| 4,281,420 | A | * | 8/1981 | Raab .............................. 128/898 |
| 4,283,799 | A | * | 8/1981 | Pratt et al. .................. 623/23.37 |
| 4,344,190 | A | * | 8/1982 | Lee et al. ......................... 606/95 |
| 4,355,428 | A | * | 10/1982 | Deloison et al. ............. 623/23.5 |
| 4,365,358 | A | * | 12/1982 | Judet et al. ................. 623/22.28 |
| 4,454,612 | A | * | 6/1984 | McDaniel et al. .......... 623/23.37 |
| 4,483,799 | A | * | 11/1984 | Kampfer et al. ................ 558/46 |
| 4,497,075 | A | * | 2/1985 | Niwa et al. .................... 424/423 |
| 4,612,160 | A | * | 9/1986 | Donlevy et al. .................... 419/2 |
| 4,644,942 | A | * | 2/1987 | Sump ......................... 623/23.55 |

(Continued)

FOREIGN PATENT DOCUMENTS

| | | |
|---|---|---|
| EP | 0501595 A1 | 9/1992 |
| WO | 0013615 A1 | 3/2000 |

(Continued)

OTHER PUBLICATIONS

PCT International Search Report, PCT/NL2007/050560 filed Nov. 12, 2007.

(Continued)

*Primary Examiner* — Alvin J. Stewart
(74) *Attorney, Agent, or Firm* — Banner & Witcoff, LTD.

(57) ABSTRACT

Kit of parts, comprising:
  a prosthesis or prosthesis part having at least one contact surface;
  metal granules having an internal porosity;
  bone cement;
  and further comprising titanium granules for use in a kit of parts, which granules preferably are osteoconductive, which granules preferably are coated with a coating from the group of osteoconductive or osteoinductive coatings, or coatings comprising bioceramic, bioglass or osteoconductive or osteoinductive molecules or fluids or cells.

77 Claims, 22 Drawing Sheets

U.S. PATENT DOCUMENTS

| | | | | |
|---|---|---|---|---|
| 4,673,409 A * | 6/1987 | Van Kampen | | 623/23.29 |
| 4,693,721 A * | 9/1987 | Ducheyne | | 623/23.54 |
| 4,713,076 A * | 12/1987 | Draenert | | 623/23.6 |
| 4,735,625 A * | 4/1988 | Davidson | | 623/23.62 |
| 4,737,411 A * | 4/1988 | Graves et al. | | 428/403 |
| 4,738,681 A * | 4/1988 | Koeneman et al. | | 623/23.35 |
| 4,755,184 A * | 7/1988 | Silverberg | | 623/23.56 |
| 4,888,022 A * | 12/1989 | Huebsch | | 623/23.19 |
| 4,888,024 A * | 12/1989 | Powlan | | 623/23.19 |
| 4,919,673 A * | 4/1990 | Willert et al. | | 623/23.48 |
| 4,950,295 A * | 8/1990 | Weigum et al. | | 623/23.48 |
| 5,007,931 A * | 4/1991 | Smith | | 623/23.3 |
| 5,015,256 A * | 5/1991 | Bruce et al. | | 128/898 |
| 5,034,186 A * | 7/1991 | Shimamune et al. | | 419/9 |
| 5,047,035 A * | 9/1991 | Mikhail et al. | | 606/93 |
| 5,133,771 A * | 7/1992 | Duncan et al. | | 623/23.2 |
| 5,171,275 A * | 12/1992 | Ling et al. | | 128/898 |
| 5,178,201 A * | 1/1993 | Ahlers | | 164/34 |
| 5,192,283 A | 3/1993 | Ling et al. | | |
| 5,192,324 A * | 3/1993 | Kenna | | 623/23.55 |
| 5,197,990 A * | 3/1993 | Lawes et al. | | 623/23.37 |
| 5,258,030 A * | 11/1993 | Wolfarth et al. | | 623/23.55 |
| 5,263,986 A * | 11/1993 | Noiles et al. | | 623/23.55 |
| 5,314,493 A * | 5/1994 | Mikhail | | 623/23.37 |
| 5,336,263 A * | 8/1994 | Ersek et al. | | 424/422 |
| 5,340,362 A * | 8/1994 | Carbone | | 623/23.19 |
| 5,343,877 A * | 9/1994 | Park | | 128/898 |
| 5,376,123 A * | 12/1994 | Klaue et al. | | 623/23.19 |
| 5,383,932 A * | 1/1995 | Wilson et al. | | 623/23.48 |
| 5,405,389 A * | 4/1995 | Conta et al. | | 623/23.55 |
| 5,425,768 A * | 6/1995 | Carpenter et al. | | 623/23.48 |
| 5,433,750 A * | 7/1995 | Gradinger et al. | | 623/23.54 |
| 5,441,537 A * | 8/1995 | Kenna | | 419/2 |
| 5,464,440 A * | 11/1995 | Johansson | | 623/23.55 |
| 5,489,306 A * | 2/1996 | Gorski | | 623/23.55 |
| 5,504,300 A * | 4/1996 | Devanathan et al. | | 219/121.64 |
| 5,507,815 A * | 4/1996 | Wagner et al. | | 623/23.5 |
| 5,571,182 A * | 11/1996 | Ersek et al. | | 623/23.73 |
| 5,571,204 A * | 11/1996 | Nies | | 623/23.19 |
| 5,589,176 A * | 12/1996 | Seare, Jr. | | 424/400 |
| 5,645,593 A * | 7/1997 | Woods et al. | | 623/23.5 |
| 5,658,338 A * | 8/1997 | Tullos et al. | | 623/22.39 |
| 5,665,121 A * | 9/1997 | Gie et al. | | 128/898 |
| 5,676,700 A * | 10/1997 | Black et al. | | 623/23.28 |
| 5,693,099 A * | 12/1997 | Harle | | 623/23.19 |
| 5,734,959 A * | 3/1998 | Krebs et al. | | 419/2 |
| 5,782,917 A * | 7/1998 | Carn | | 623/23.48 |
| 5,855,612 A * | 1/1999 | Ohthuki et al. | | 424/423 |
| 5,861,042 A * | 1/1999 | Buechel et al. | | 128/898 |
| 5,868,796 A * | 2/1999 | Buechel et al. | | 623/16.11 |
| 5,947,893 A * | 9/1999 | Agrawal et al. | | 600/36 |
| 5,954,771 A * | 9/1999 | Richelsoph et al. | | 623/23.15 |
| 5,976,188 A * | 11/1999 | Dextradeur et al. | | 623/23.23 |
| 6,008,432 A * | 12/1999 | Taylor | | 623/23.3 |
| 6,066,176 A * | 5/2000 | Oshida | | 623/23.62 |
| 6,087,553 A * | 7/2000 | Cohen et al. | | 623/22.21 |
| 6,120,544 A * | 9/2000 | Grundei et al. | | 623/23.14 |
| 6,123,731 A * | 9/2000 | Boyce et al. | | 623/23.63 |
| 6,136,038 A * | 10/2000 | Raab | | 623/23.37 |
| 6,136,369 A | 10/2000 | Leitao et al. | | |
| 6,149,689 A * | 11/2000 | Grundei | | 623/23.5 |
| 6,193,761 B1 * | 2/2001 | Treacy | | 623/23.55 |
| 6,206,924 B1 * | 3/2001 | Timm | | 623/17.16 |
| 6,214,053 B1 * | 4/2001 | Ling et al. | | 623/23.11 |
| 6,312,473 B1 * | 11/2001 | Oshida | | 623/23.55 |
| 6,395,327 B1 * | 5/2002 | Shetty | | 427/2.26 |
| 6,447,550 B1 * | 9/2002 | Hunter et al. | | 623/22.15 |
| 6,478,825 B1 * | 11/2002 | Winterbottom et al. | | 623/23.63 |
| 6,485,521 B1 * | 11/2002 | Say et al. | | 623/23.55 |
| 6,497,728 B2 * | 12/2002 | Yong | | 623/23.46 |
| 6,524,344 B2 * | 2/2003 | Yoon | | 623/23.46 |
| 6,537,320 B1 * | 3/2003 | Michelson | | 623/17.11 |
| 6,565,606 B1 * | 5/2003 | Bruce et al. | | 623/23.63 |
| 6,582,470 B1 * | 6/2003 | Lee et al. | | 623/23.55 |
| 6,699,288 B2 * | 3/2004 | Moret | | 623/17.16 |
| 6,746,488 B1 * | 6/2004 | Bales | | 623/23.51 |
| 6,802,863 B2 * | 10/2004 | Lawson et al. | | 623/17.16 |
| 6,926,741 B2 * | 8/2005 | Kolb | | 623/23.48 |
| 6,979,336 B2 * | 12/2005 | Durniak | | 606/92 |
| 6,981,991 B2 * | 1/2006 | Ferree | | 623/23.46 |
| 7,044,978 B2 * | 5/2006 | Howie et al. | | 623/23.48 |
| 7,048,870 B1 * | 5/2006 | Ellingsen et al. | | 216/109 |
| 7,052,518 B2 * | 5/2006 | Irie et al. | | 623/23.56 |
| 7,056,577 B1 | 6/2006 | Bruce et al. | | |
| 7,083,651 B2 * | 8/2006 | Diaz et al. | | 623/17.13 |
| 7,208,222 B2 * | 4/2007 | Rolfe et al. | | 428/304.4 |
| 7,211,113 B2 * | 5/2007 | Zelener et | | 623/22.43 |
| 7,229,478 B2 * | 6/2007 | Masini | | 623/19.11 |
| 7,258,810 B2 * | 8/2007 | Hunter et al. | | 216/41 |
| 7,368,065 B2 * | 5/2008 | Yang et al. | | 216/83 |
| 7,393,361 B2 * | 7/2008 | Zubok et al. | | 623/17.15 |
| 7,491,219 B2 * | 2/2009 | Steinberg | | 606/279 |
| 7,501,073 B2 * | 3/2009 | Wen et al. | | 216/109 |
| 7,534,451 B2 * | 5/2009 | Erbe et al. | | 424/484 |
| 7,550,009 B2 * | 6/2009 | Arnin et al. | | 623/17.15 |
| 7,553,539 B2 * | 6/2009 | Bruce et al. | | 428/312.8 |
| 7,563,286 B2 * | 7/2009 | Gerber et al. | | 623/17.14 |
| 7,635,447 B2 * | 12/2009 | Hamman et al. | | 419/2 |
| 7,648,735 B2 * | 1/2010 | Hunter et al. | | 427/248.1 |
| 7,776,099 B2 * | 8/2010 | Lococo | | 623/23.48 |
| 7,828,805 B2 * | 11/2010 | Hoag et al. | | 606/89 |
| 7,842,095 B2 * | 11/2010 | Klein | | 623/23.19 |
| 7,857,860 B2 * | 12/2010 | Saini et al. | | 623/23.56 |
| 7,993,402 B2 * | 8/2011 | Sidler | | 623/17.11 |
| 8,066,778 B2 * | 11/2011 | Meridew et al. | | 623/22.32 |
| 8,075,680 B2 * | 12/2011 | Mongiorgi et al. | | 106/35 |
| 8,197,550 B2 * | 6/2012 | Brown et al. | | 623/22.32 |
| 2001/0004711 A1 * | 6/2001 | Lazzara et al. | | 623/23.5 |
| 2001/0004712 A1 * | 6/2001 | Ling et al. | | 623/23.25 |
| 2001/0020187 A1 * | 9/2001 | Guettinger et al. | | 623/23.25 |
| 2002/0128721 A1 * | 9/2002 | Chan | | 623/23.48 |
| 2002/0151983 A1 * | 10/2002 | Shetty | | 623/23.5 |
| 2002/0156529 A1 | 10/2002 | Li et al. | | |
| 2002/0173855 A1 * | 11/2002 | Mansmann | | 623/23.72 |
| 2002/0183851 A1 * | 12/2002 | Spiegelberg et al. | | 623/22.12 |
| 2003/0004578 A1 * | 1/2003 | Brown et al. | | 623/23.72 |
| 2003/0055511 A1 * | 3/2003 | Schryver et al. | | 623/23.5 |
| 2003/0060873 A1 | 3/2003 | Gertner et al. | | |
| 2003/0163205 A1 * | 8/2003 | Lawson | | 623/23.48 |
| 2003/0191533 A1 * | 10/2003 | Dixon et al. | | 623/17.14 |
| 2003/0229399 A1 * | 12/2003 | Namavar | | 623/23.53 |
| 2004/0019132 A1 * | 1/2004 | Long et al. | | 523/115 |
| 2004/0107002 A1 * | 6/2004 | Katsuya | | 623/23.25 |
| 2004/0149586 A1 * | 8/2004 | Sul | | 205/171 |
| 2004/0157952 A1 * | 8/2004 | Soffiati et al. | | 523/115 |
| 2004/0167632 A1 * | 8/2004 | Wen et al. | | 623/23.5 |
| 2004/0176854 A1 * | 9/2004 | Hesseling et al. | | 623/23.48 |
| 2004/0199261 A1 * | 10/2004 | Jones | | 623/23.5 |
| 2004/0243133 A1 * | 12/2004 | Materna | | 606/76 |
| 2005/0013973 A1 * | 1/2005 | Richter et al. | | 428/158 |
| 2005/0027366 A1 * | 2/2005 | Saini et al. | | 623/23.5 |
| 2005/0112397 A1 * | 5/2005 | Rolfe et al. | | 428/593 |
| 2005/0123672 A1 * | 6/2005 | Justin et al. | | 427/2.26 |
| 2005/0129778 A1 | 6/2005 | Mulye | | |
| 2005/0159820 A1 * | 7/2005 | Yoshikawa et al. | | 623/23.5 |
| 2005/0161120 A1 * | 7/2005 | Inagaki et al. | | 148/220 |
| 2005/0165494 A1 * | 7/2005 | McLeod et al. | | 623/23.26 |
| 2005/0167309 A1 * | 8/2005 | Iwatschenko | | 206/438 |
| 2005/0177162 A1 | 8/2005 | McLeod et al. | | |
| 2005/0234557 A1 * | 10/2005 | Lambrecht et al. | | 623/17.16 |
| 2005/0273176 A1 * | 12/2005 | Ely et al. | | 623/22.32 |
| 2006/0015187 A1 * | 1/2006 | Hunter et al. | | 623/23.5 |
| 2006/0078847 A1 * | 4/2006 | Kwan | | 433/174 |
| 2006/0122706 A1 * | 6/2006 | Lo | | 623/23.5 |
| 2006/0129161 A1 * | 6/2006 | Amrich et al. | | 606/85 |
| 2006/0178751 A1 * | 8/2006 | Despres et al. | | 623/23.5 |
| 2006/0229715 A1 * | 10/2006 | Istephanous et al. | | 623/1.46 |
| 2006/0235541 A1 * | 10/2006 | Hodorek | | 623/23.51 |
| 2007/0173952 A1 * | 7/2007 | Hermansson et al. | | 623/23.76 |
| 2007/0282455 A1 * | 12/2007 | Luginbuehl et al. | | 623/23.72 |
| 2008/0011613 A1 * | 1/2008 | Wang | | 205/318 |
| 2008/0195232 A1 * | 8/2008 | Carr-Brendel et al. | | 623/23.76 |
| 2009/0112315 A1 * | 4/2009 | Fang et al. | | 623/11.11 |
| 2009/0162235 A1 * | 6/2009 | Kita et al. | | 419/2 |
| 2009/0187256 A1 * | 7/2009 | Raugth et al. | | 623/23.55 |
| 2009/0192610 A1 * | 7/2009 | Case et al. | | 623/16.11 |
| 2009/0270998 A1 * | 10/2009 | Kokubo et al. | | 623/23.55 |

| | | | |
|---|---|---|---|
| 2010/0075419 A1* | 3/2010 | Inagaki et al. ............... 435/402 |
| 2010/0094430 A1* | 4/2010 | Krumdieck ................. 623/23.5 |
| 2010/0121463 A1* | 5/2010 | Tormala et al. ............ 623/23.75 |
| 2010/0131074 A1* | 5/2010 | Shikinami ................. 623/23.5 |
| 2010/0168869 A1* | 7/2010 | Long et al. ................ 623/23.72 |
| 2010/0179667 A1* | 7/2010 | Day et al. .................. 623/23.72 |
| 2010/0222892 A1* | 9/2010 | Linares ...................... 623/23.5 |
| 2011/0022180 A1* | 1/2011 | Melkent et al. ............ 623/23.5 |
| 2011/0022181 A1* | 1/2011 | Kasahara et al. ........... 623/23.5 |

FOREIGN PATENT DOCUMENTS

| | | |
|---|---|---|
| WO | 2006033623 A1 | 3/2006 |
| WO | 2006121330 A2 | 11/2006 |
| WO | 2006121330 A3 | 11/2006 |
| WO | 2008056987 A2 | 5/2008 |

OTHER PUBLICATIONS

Verdonschot N, Van Hal CT, Schreurs BW, Buma P, Huiskes R, Slooff TJ. "Time-dependent Mechanical Properties of HA/TCP Particles in Relation to Morsellized Bone Grafts for Use in Impaction Grafting" J. Biomed. Mater. Res. 2001; 58(5); 599-604.

Yan WQ, Nakamura T, Kawanabe K, Nishigochi S, Oka M, Kokubo T. "Apatite Layer Coated Titanium for Use as Bone Bonding Implants" Biomaterials 1997; 18:1185-1190 (The coating has been applied by Biomaterialen, Radbout University, Nijmegan).

Arts JJ, Gardeniers JW, Welten ML, Verdonschot N, Schreurs BW, Buma P. "No Negative Effects of Bone Impaction Grafting with Bone and Ceramic Mixtures" Clin Orthop 2005; 438: 239-247.

Buma P, Arts JJ, Gardeniers JW, Verdonschot N, Schreuers BW. "No Effect of Bone Morphogentic Protein-7 (OP-1) on the Incorporation of Impacted Bone Grafts in a Realistic Acetabular Model" J. Biomed Mater Res B Appl Biomater 2007.

Schimmel JW, Buma P, Versleyen D, Huiskes R, Slooff TJ. "Acetabular Reconstruction with Impacted Morselized Cancellous Allografts in Cemented Hip Arthroplasty: A Histological and Biomechanical Study on the Goat" J. Anthroplasty 1998; 13:438-448.

* cited by examiner

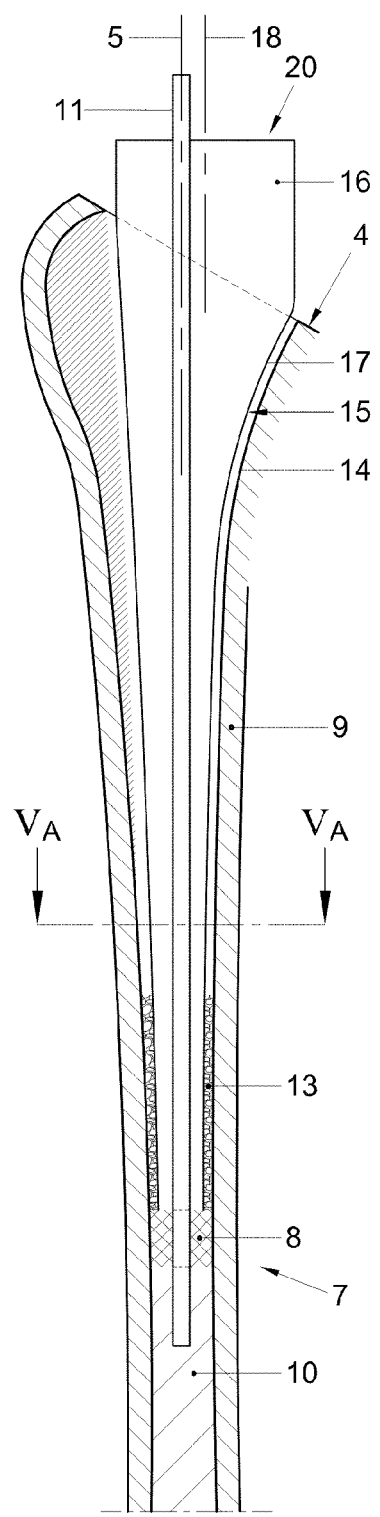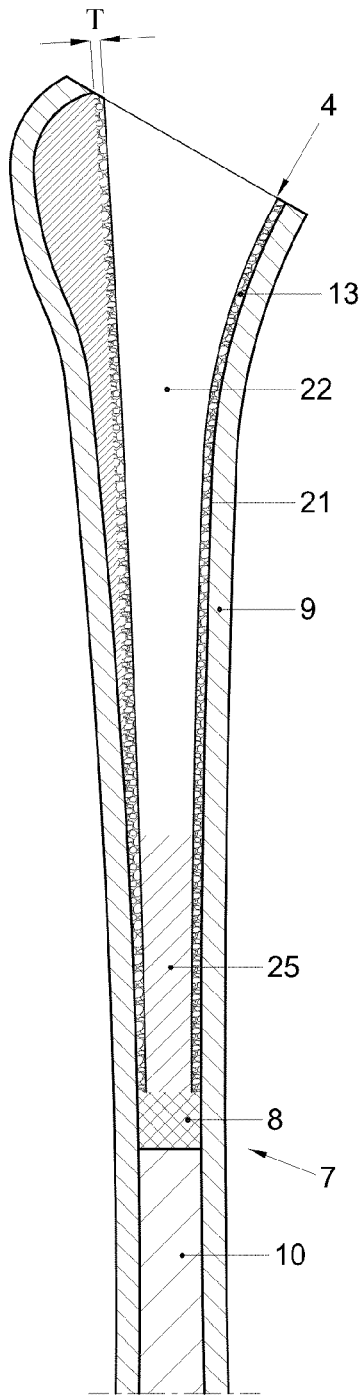
Fig. 5
Fig. 5A
Fig. 6

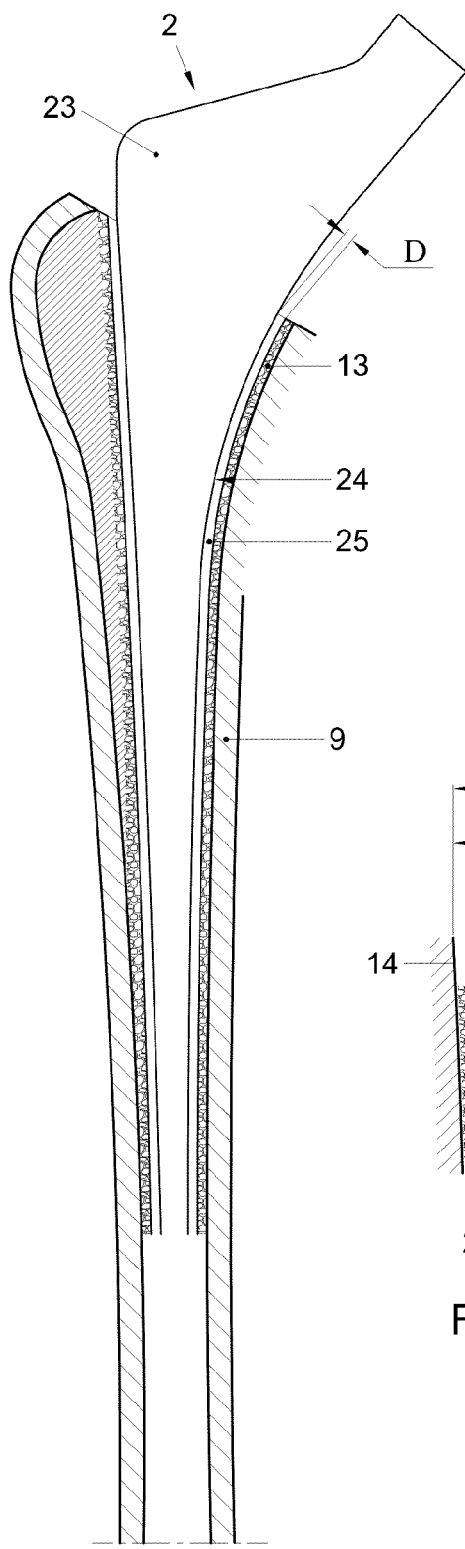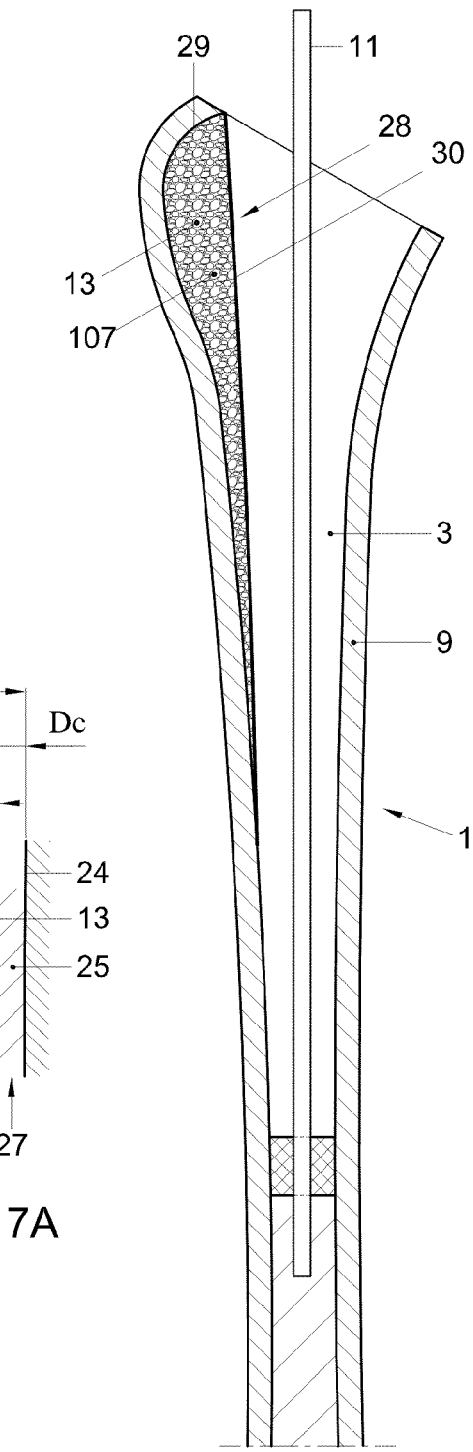
Fig. 7
Fig. 7A
Fig. 8

KIT AND METHOD FOR FIXATING A PROSTHESIS OR PART THEREOF AND/OR FILLING OSSEOUS DEFECTS

RELATED APPLICATIONS

This application is a continuation of PCT/NL2007/050560, designating the United States and filed Nov. 12, 2007, which claims the benefit of the filing date of Netherland application no. 1032851 filed Nov. 10, 2006; each of which is hereby incorporated herein by reference in the entirety for all purposes.

The invention relates to means for fixating a prosthesis or part thereof and/or filling osseous defects.

BACKGROUND

In prosthetic fixation such as hip replacements a part of an existing bone is removed, providing a fixating surface, for example by drilling and/or reaming a hole in the remaining bone. A prosthesis is then fixed to said surface, providing for a stable configuration and replacement of a joint.

For fixating said prosthesis to said surface various means and techniques are known and commonly used. At present these techniques can roughly be divided into cemented and non-cemented prosthesis. Cemented prosthesis are fixated to a fixating surface using a layer of bone cement, for example a cement based on polymethyl metacrylate. The cement adheres both to the prosthesis and to the fixating surface. In non-cemented techniques various means can be used, such as clamping means, screws and the like, which mechanically fixate the prosthesis to and/or through the bone. A different approach is to allow bone and other tissue to grow onto and/or into a prosthesis. To this end a part of the prosthesis can be provided with a bone growth stimulating and bone adhering coating. Initially after fixation a person or animal having received the prosthesis will be allowed to load the joint only to a limited extend.

It is also known to use bone chips which are provided as a layer between the fixating surface and a part of the prosthesis, after which bone and other tissue is allowed to grow into said layer of bone chips. Such method is for example described in U.S. Pat. No. 5,047,035. In this known technique, which is normally in hip prosthesis replacement surgery, a layer of bone chips harvested from the patient or from a donor bank is provided in a bore in a femur, after which a compacting device is inserted in said bore, which is used for compacting said layer against the wall of said bore. Then a layer of cement is provided inside an opening in said layer which results from removing said device after compacting. A stem of a prosthesis is then positioned within said layer of bone cement, fixating said prosthesis.

A problem in revision surgery as described above is bone stock loss. Bone stock restoration is one of the key factors in long-term stability of implants such as prosthesis, especially in revision surgery. To this end bone impaction grafting (BIG), using bone chips which are impacted in to bone defects, as disclosed above, has proven promising because it restores the original bone stock. For BIG only human allograft and some autograft bone chips are used. Xenografts may be considered but currently are used on a very small scale for different reasons. One of the problems of this technique is a shortage of allograft bone chips as a result of the strongly increased and still increasing number of arthroplasties. Moreover, the application of allografts and xenografts has the potential hazard of disease transmission and rejection by the recipient. Furthermore, religious or other convictions can be a potential obstacle for the application thereof.

From WO 00/13615 it is known to use a pouch filled with a batch of a mixture of porous granules of tissue compatible material and disintegrated tissue-compatible biological material such as bone meal, to which mixture a further tissue-compatible component has been added which allows modelling or moulding of the mixture within the pouch. The pouch is vibrated in order to obtain sufficient compacting of the mixture before use. In vivo bone and other tissue is allowed to grow into said pouch and into said mixture, for obtaining a desired fixation. Loading of the prosthesis directly after placement should be avoided. Use of the pouches is difficult, especially during placement in relatively narrow, deep holes such as for fixating a femoral component. Moreover, still allograft, autograft and/or xenograft bone chips have to be made available.

A goal of the present invention is to provide an alternative means and technique for fixating a prosthesis or part thereof and/or filling osseous defects.

A further goal of the present invention is to overcome at least one of the drawbacks of at least one of the techniques described here above.

A further goal of the present invention is to provide a kit of parts, suitable for prosthesis fixation, especially but not exclusively in revision surgery.

A still further goal of the present invention is to provide for a method for fixating a prosthesis or part thereof and/or filling osseous defects.

SUMMARY

In a first aspect of the present invention a kit of parts is provided comprising a prosthesis or prosthesis part having at least one contact surface, metal granules having an internal porosity and bone cement. Preferably said kit of parts also comprises compacting means for compacting a layer of said granules inside a natural or artificial opening in a human or animal, natural or artificial bone, in vivo or in vitro, leaving an opening for said prosthesis or part thereof and a layer of bone cement extending between said contact surface and said layer of granules.

In a second aspect of the invention a kit of parts is provided comprising titanium based, porous granules wherein at least 50% of said granules by volume have an average size between 1 and 10 mm, more specifically between 2.5 and 7 mm. Preferably substantially all granules have an average size within said ranges. In another aspect the granules have an average porosity of 40-90%.

In a still further aspect of the present invention said granules are coated, preferably with a coating comprising calcium phosphate. The coating can have an average thickness between 0.5 and 100 micrometer.

In another aspect of the present invention the granules are or have been soaked in a fluid, preferably before insertion into an opening in a bone. Said fluid may consist of for instance of a 0.9% saline solution or body fluids like blood or serum or bone marrow.

In different defects or different parts of a human or animal body different sizes of granules may be used. For example, in femoral reconstructions smaller granules could be used than in acetabular reconstructions.

DETAILED DESCRIPTION

The present invention shall be elucidated further, referring to the drawings, wherein:

FIG. 5 shows schematically the femur according to FIG. 4, wherein a compacting device is placed over the guide wire and forced into the granules;

FIG. 6 shows schematically the femur according to FIG. 5, wherein a layer of granules is formed against the inside wall of said opening, wherein bone cement is provided most distally in said opening;

FIG. 7 shows schematically the femur according to FIG. 6, wherein a femoral component is driven into said bone cement, forcing said cement between said layer of granules and a contact surface of said femoral component and into said layer of granules;

FIG. 8 shows part of a femur in which an osseous defect is filled with granules and a mesh;

FIG. 9A-D microscopic images of granules according to the present invention, at magnifications of 10, 50, 500 and 2000 times respectively.

Figure 10A:
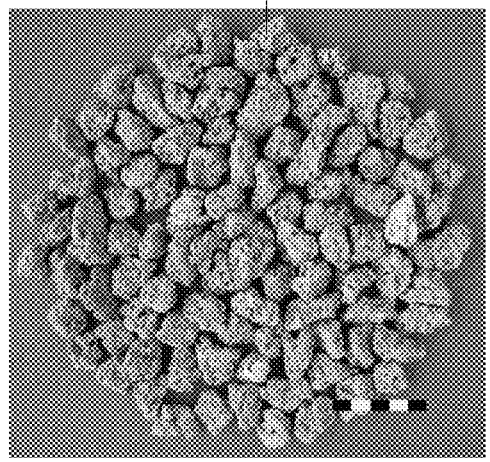
Figure 10B:
Figure 10C:
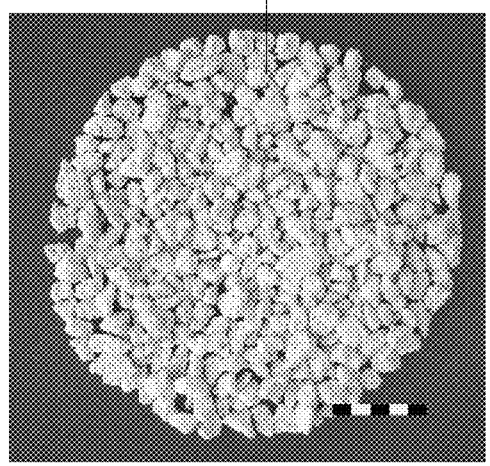
Figure 10D:
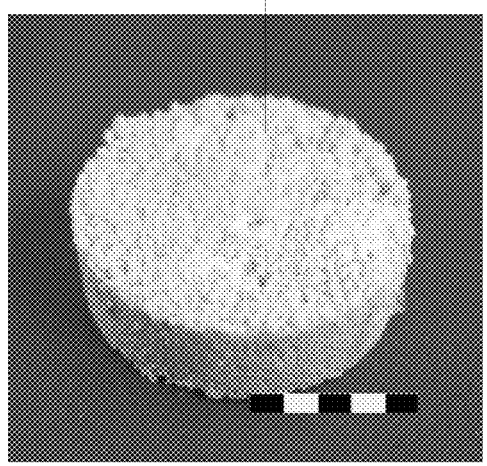
Figure 10E:
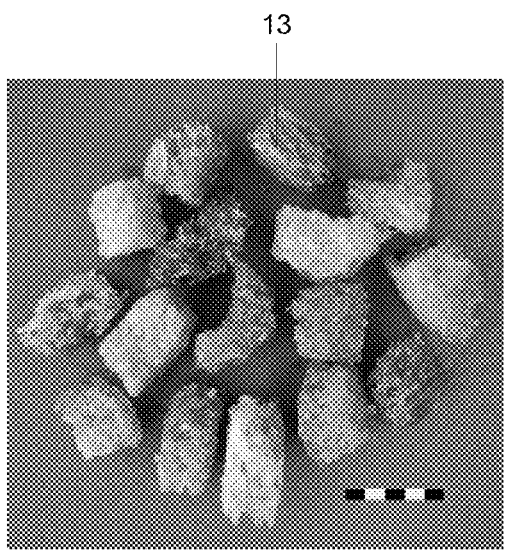
Figure 10F:
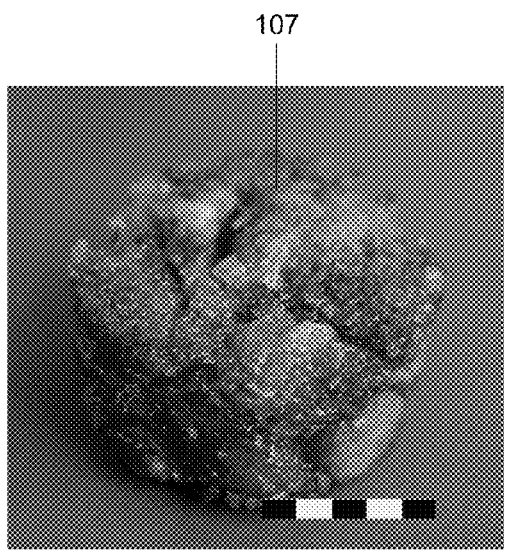
Figure 11:
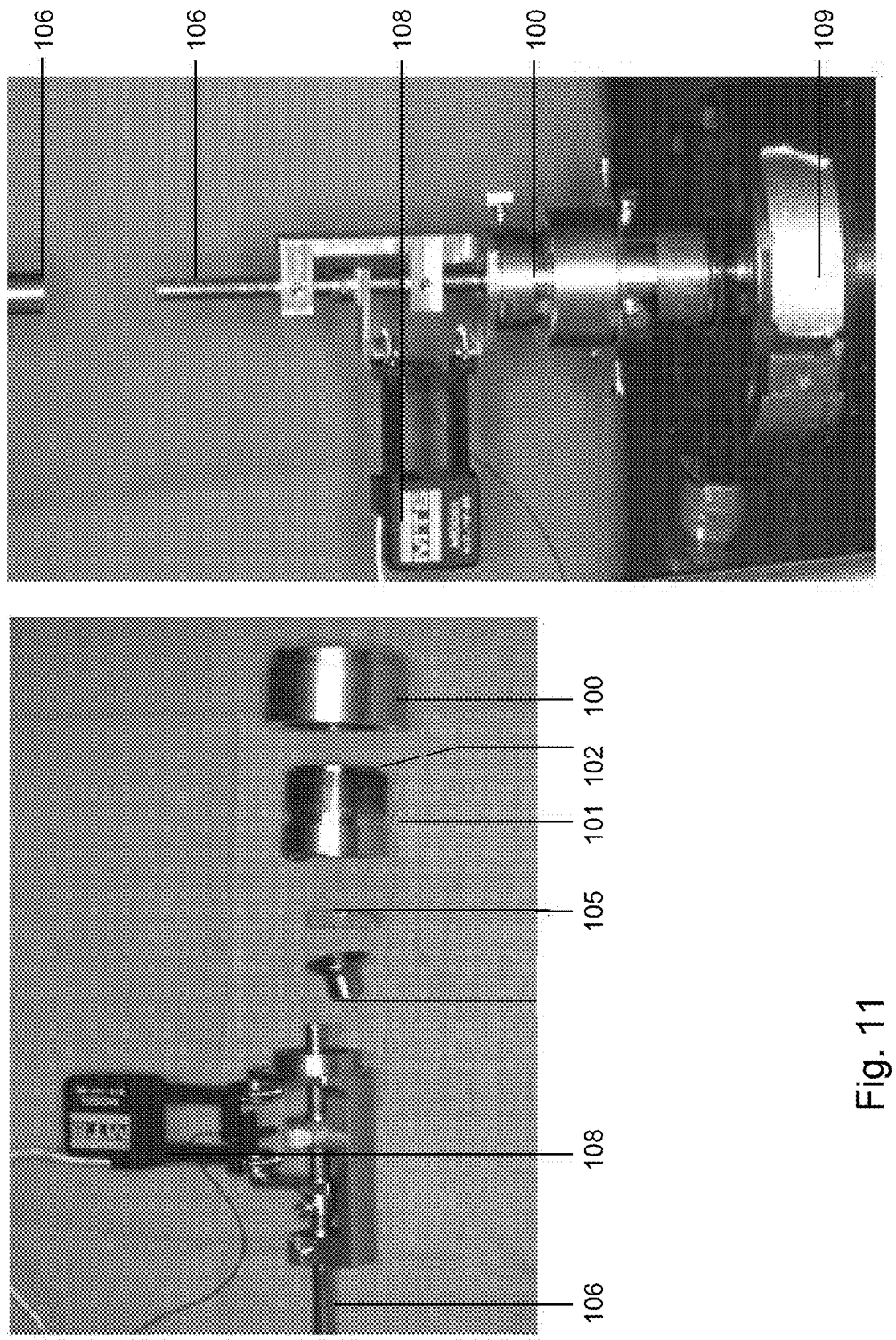
Figure 12:
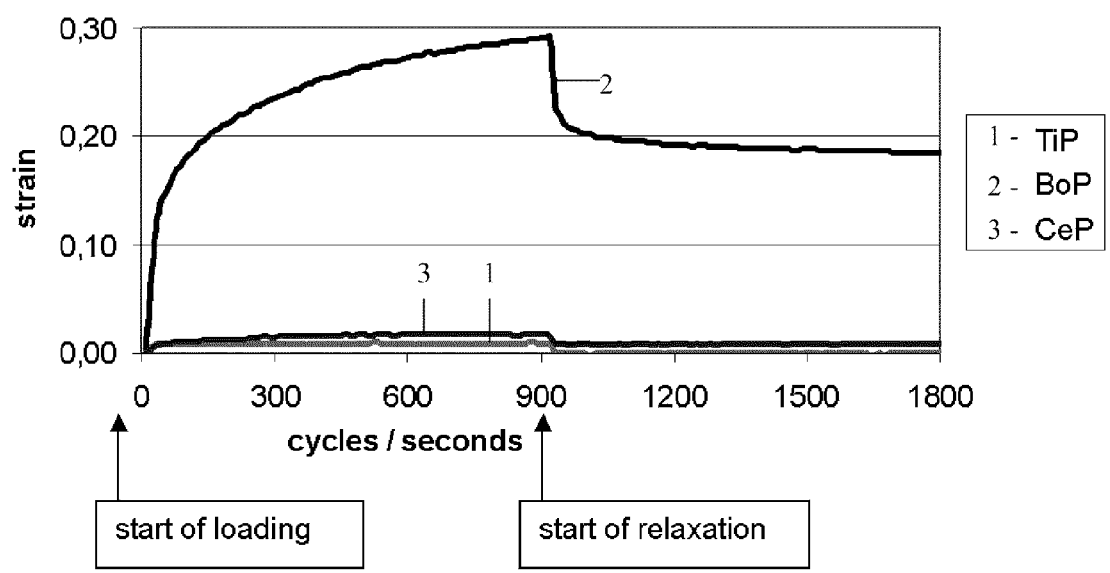

FIG. 10A-B granules according to the present invention prior to and after impaction according to the invention;

FIG. 10C-F ceramic particles (CeP) and cancellous human bone chips (BoP) prior to and after impaction according to the invention, as reference material;

FIG. 11 testing equipment used for in vitro testing the granules according to the present invention and the reference particles; and FIG. 12 a strain curve for the compacted granules and particles of FIGS. 10B, D and F.

Figure 13A:
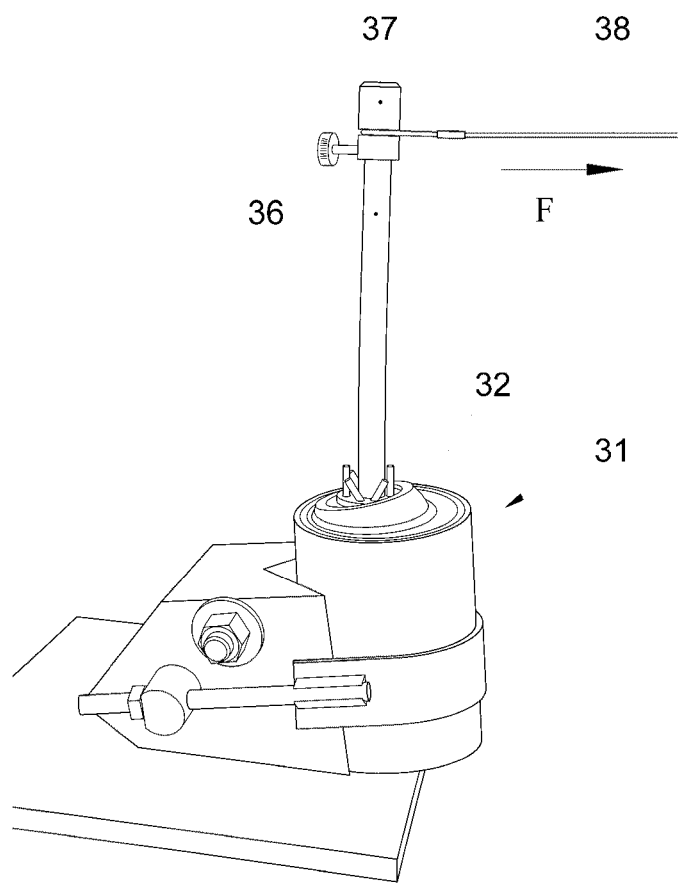
Figure 13C:
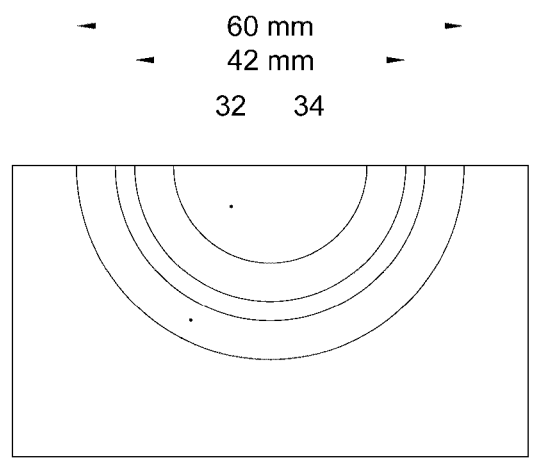
Figure 13B:
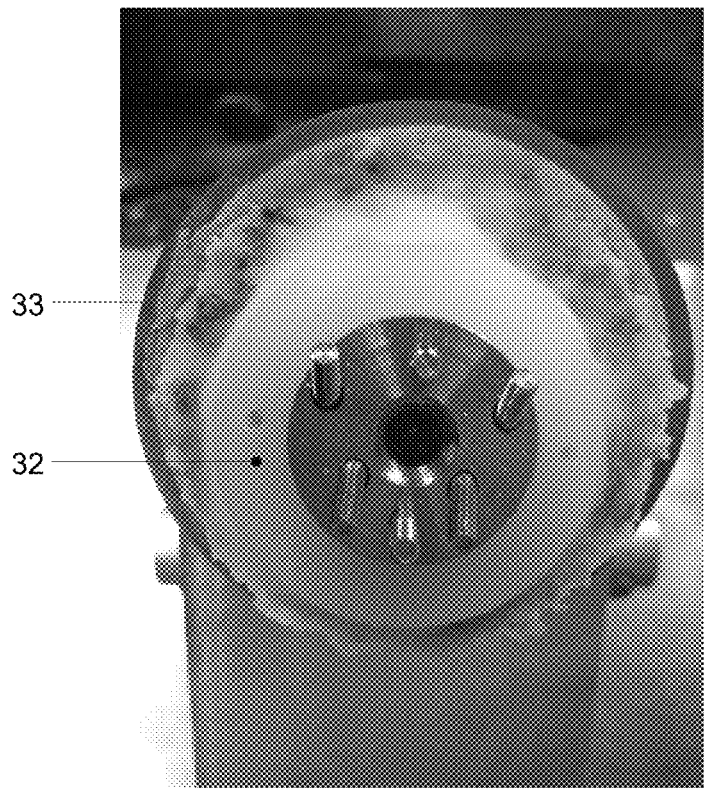
Figure 14:
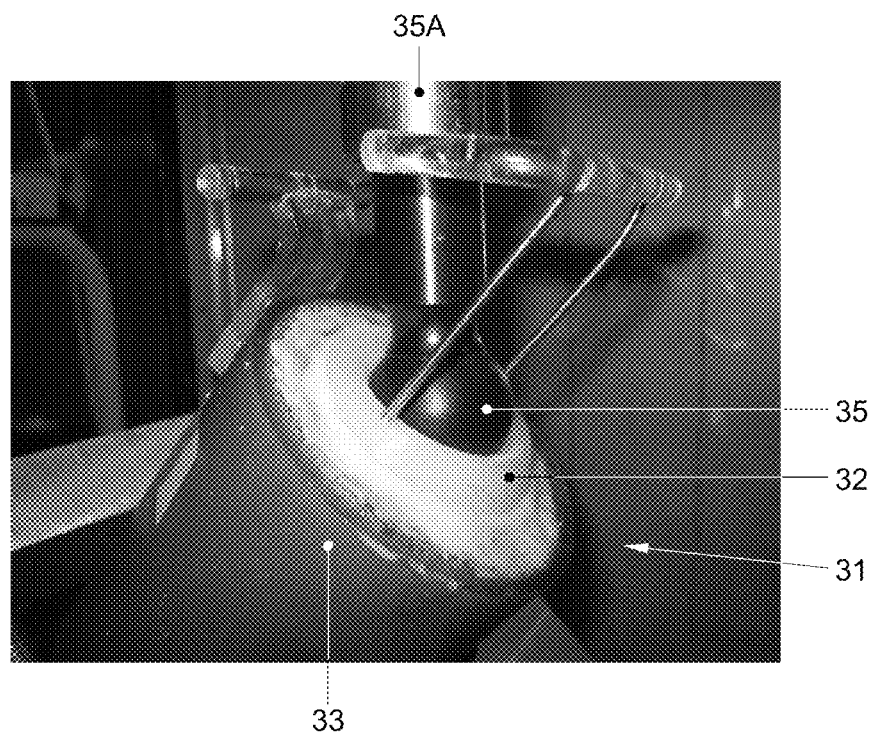
Figure 14A:
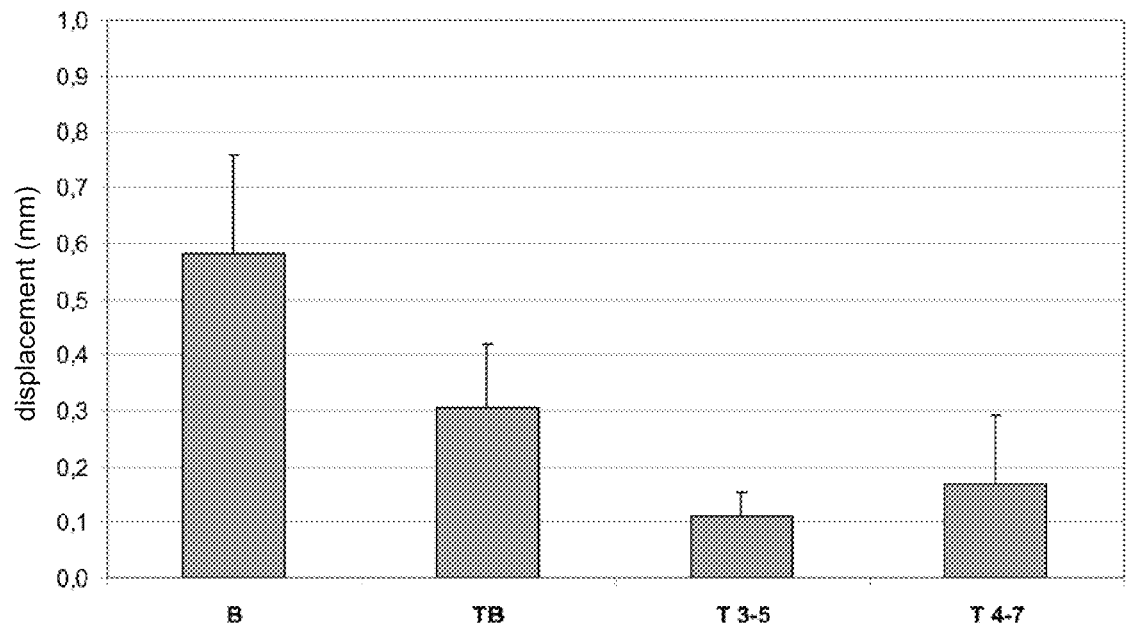
Figure 14A:
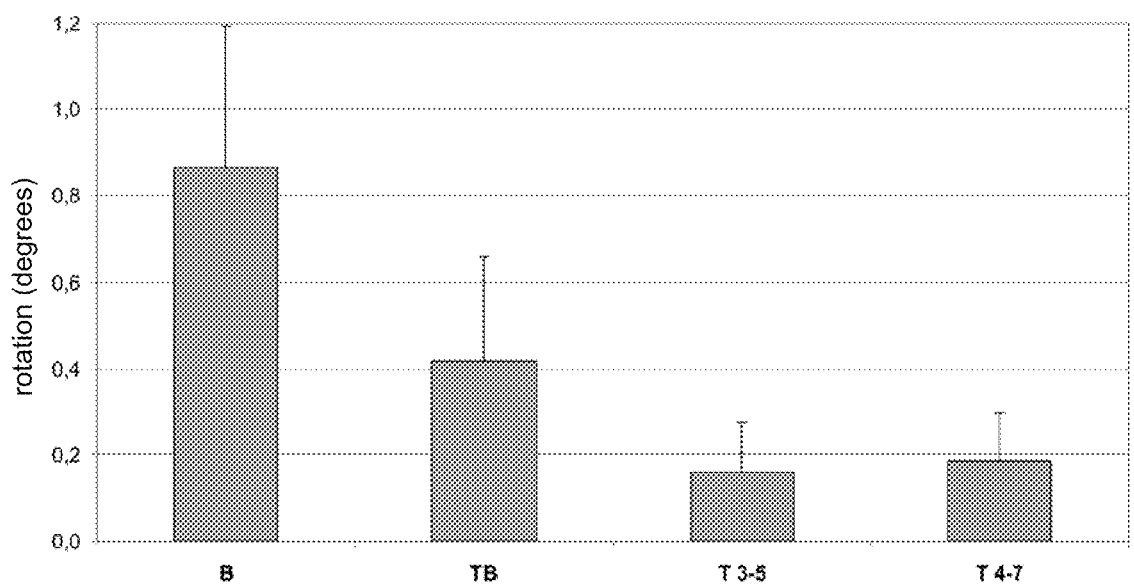
Figure 14B:
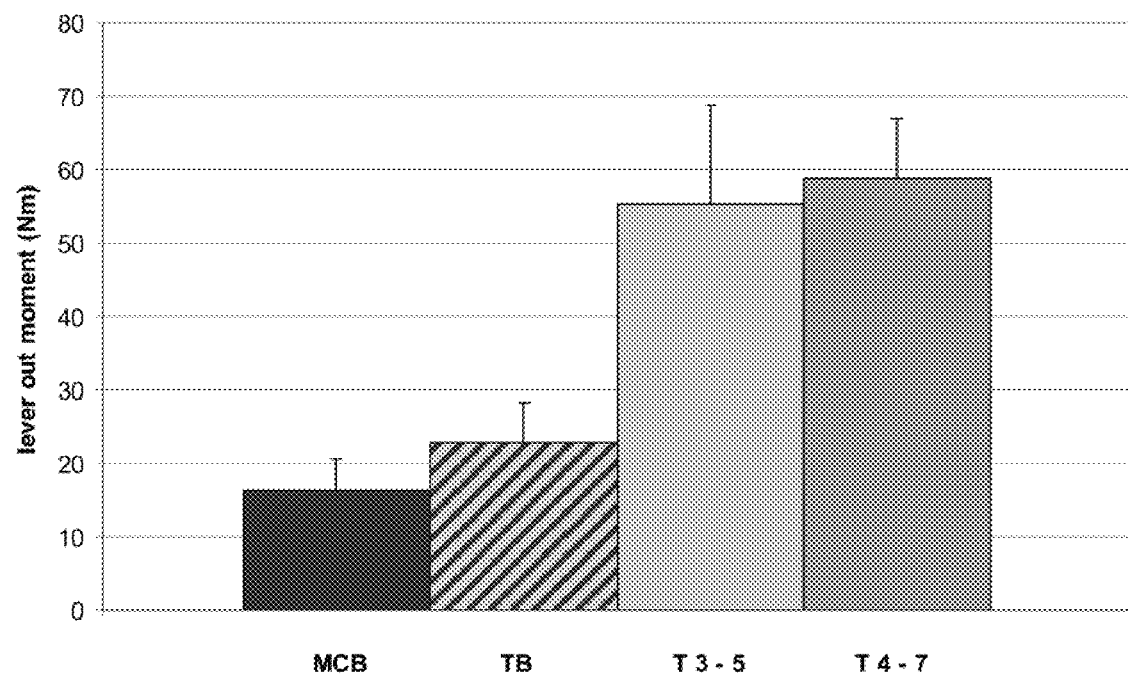
Figure 14C:
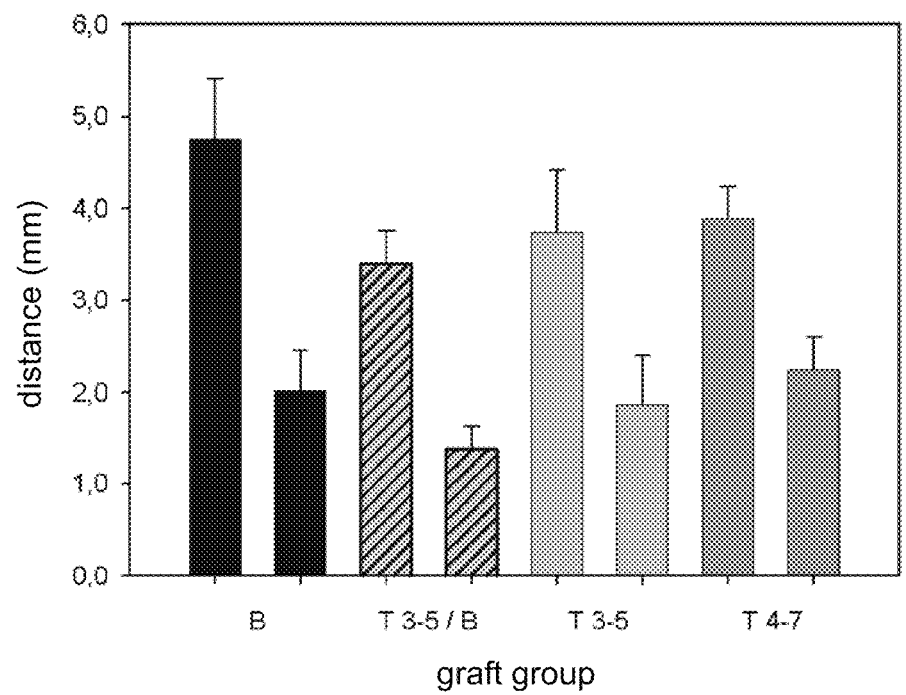
Figure 15:
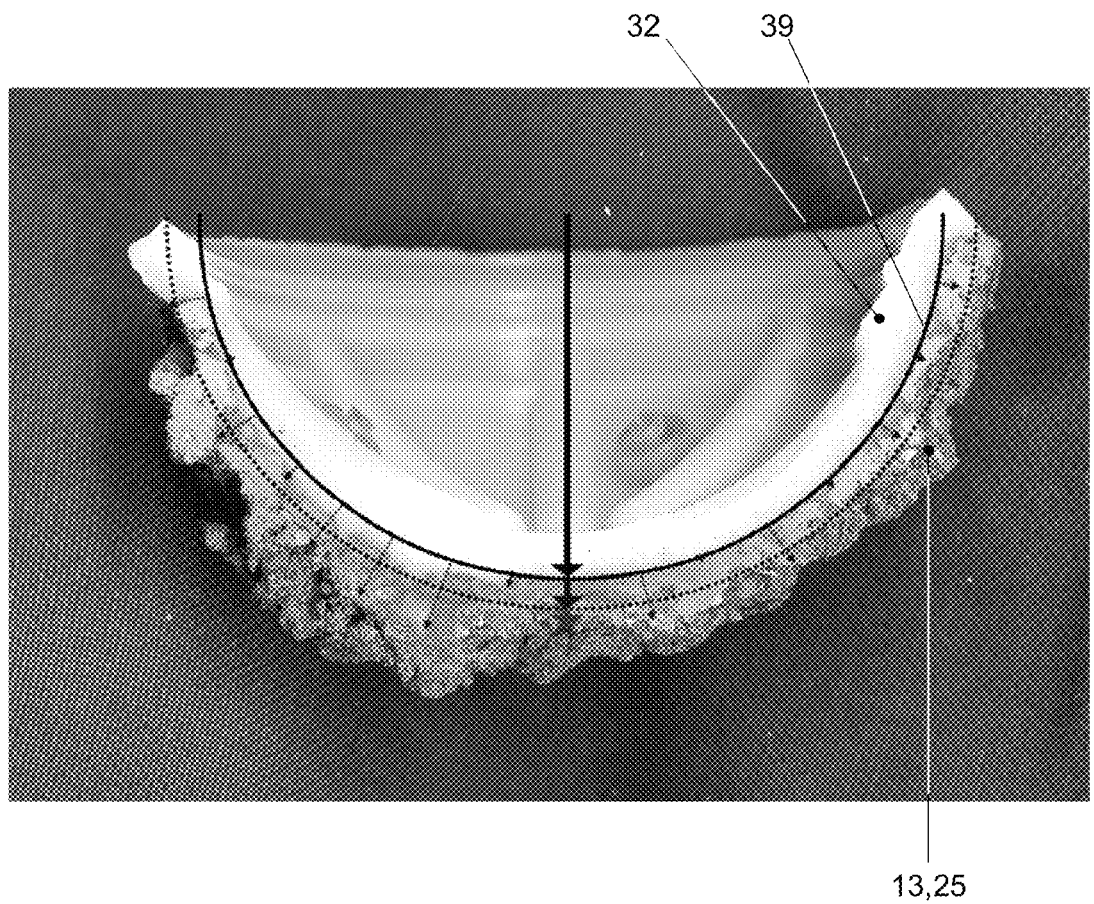
Figure 16:
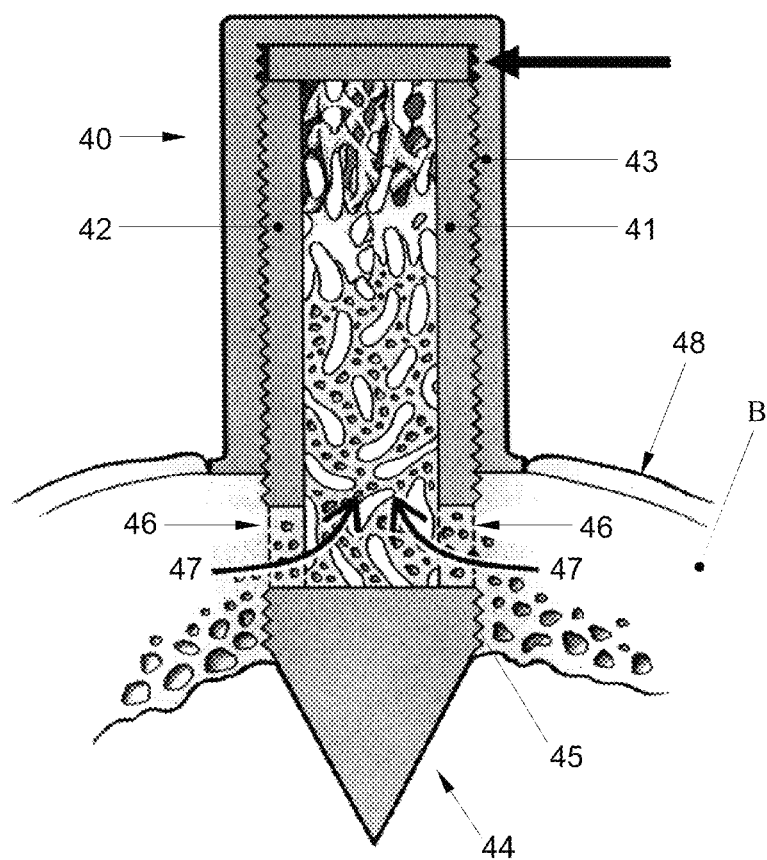
Figure 17:
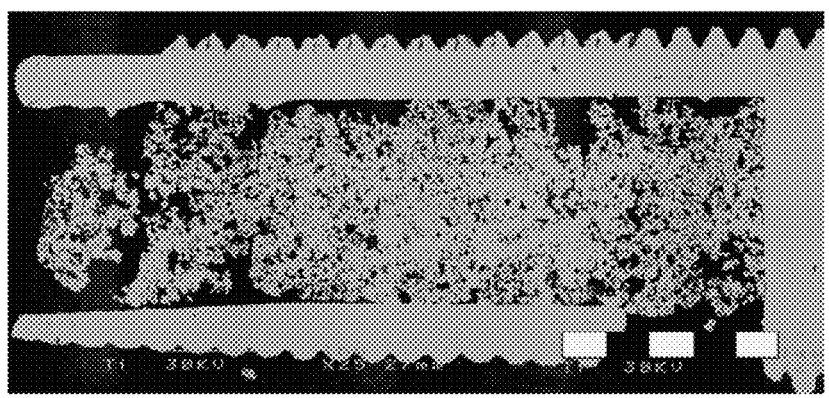
Figure 18:
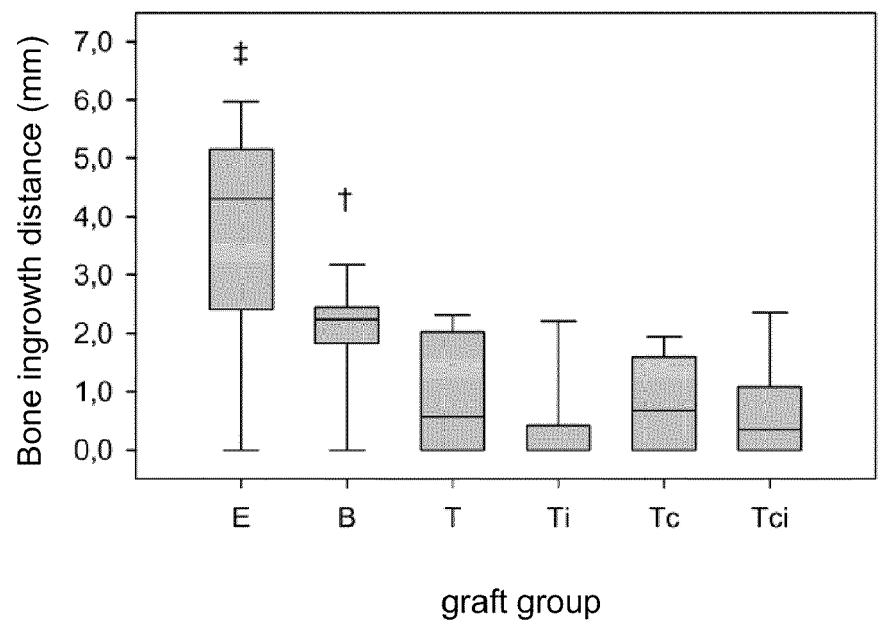
Figure 19:
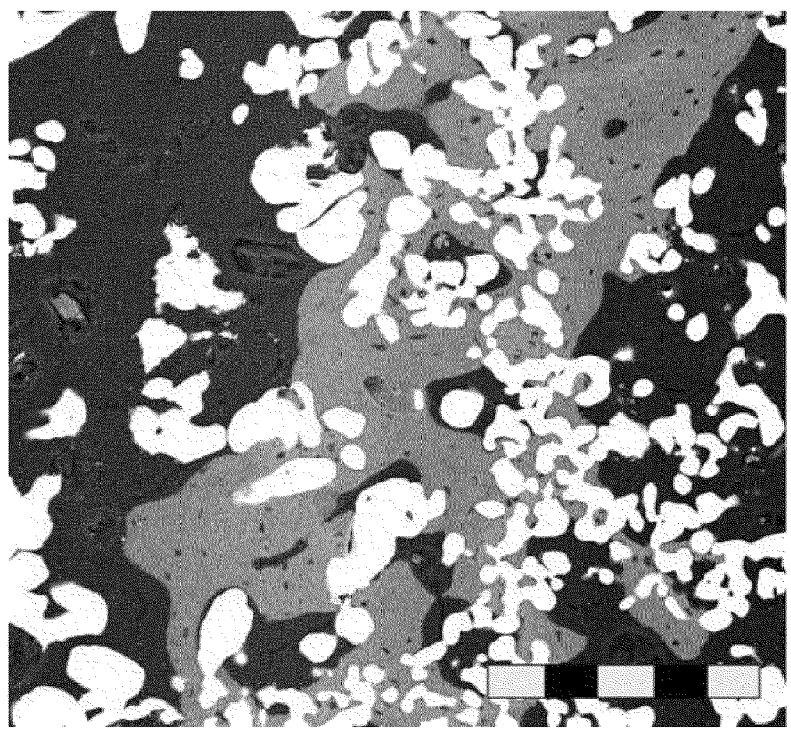
Figure 20:
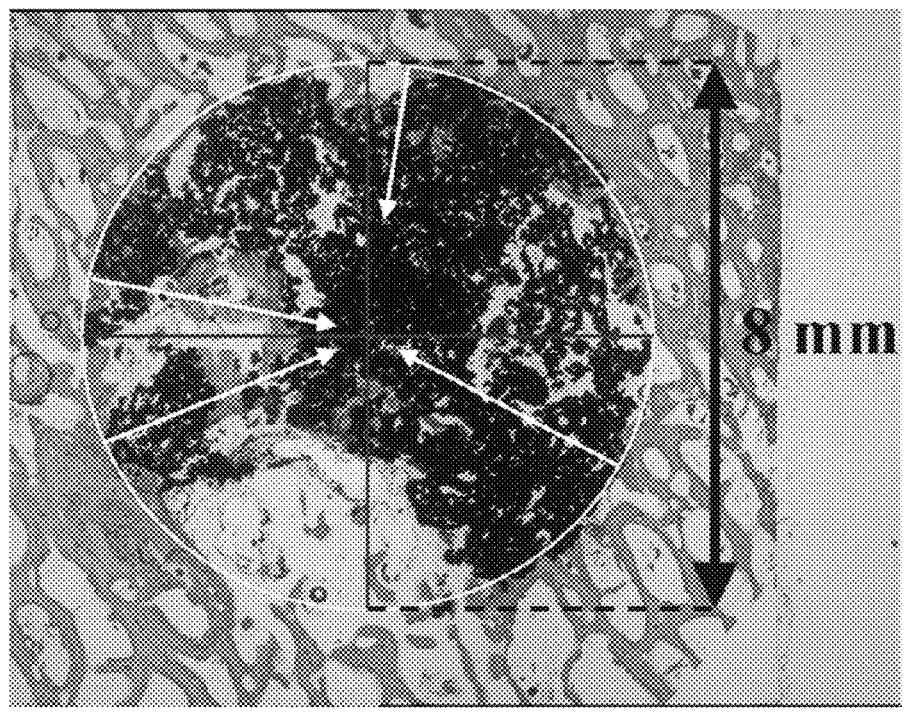
Figure 21:
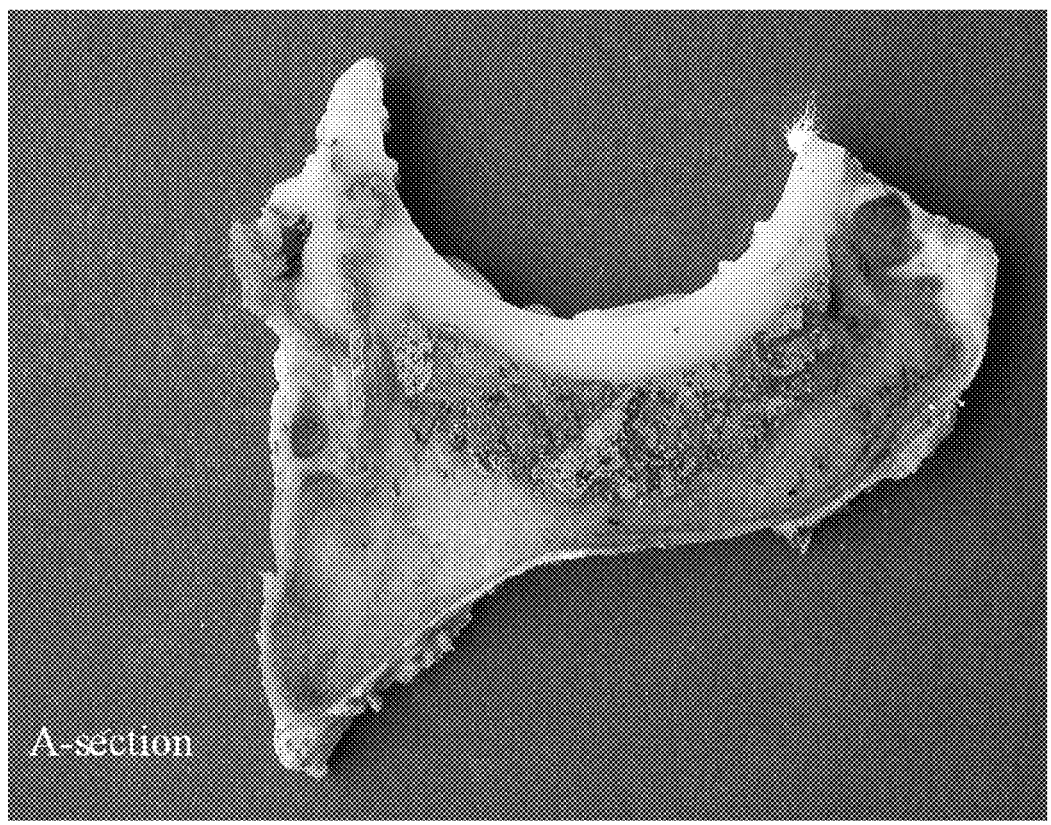
Figure 22:
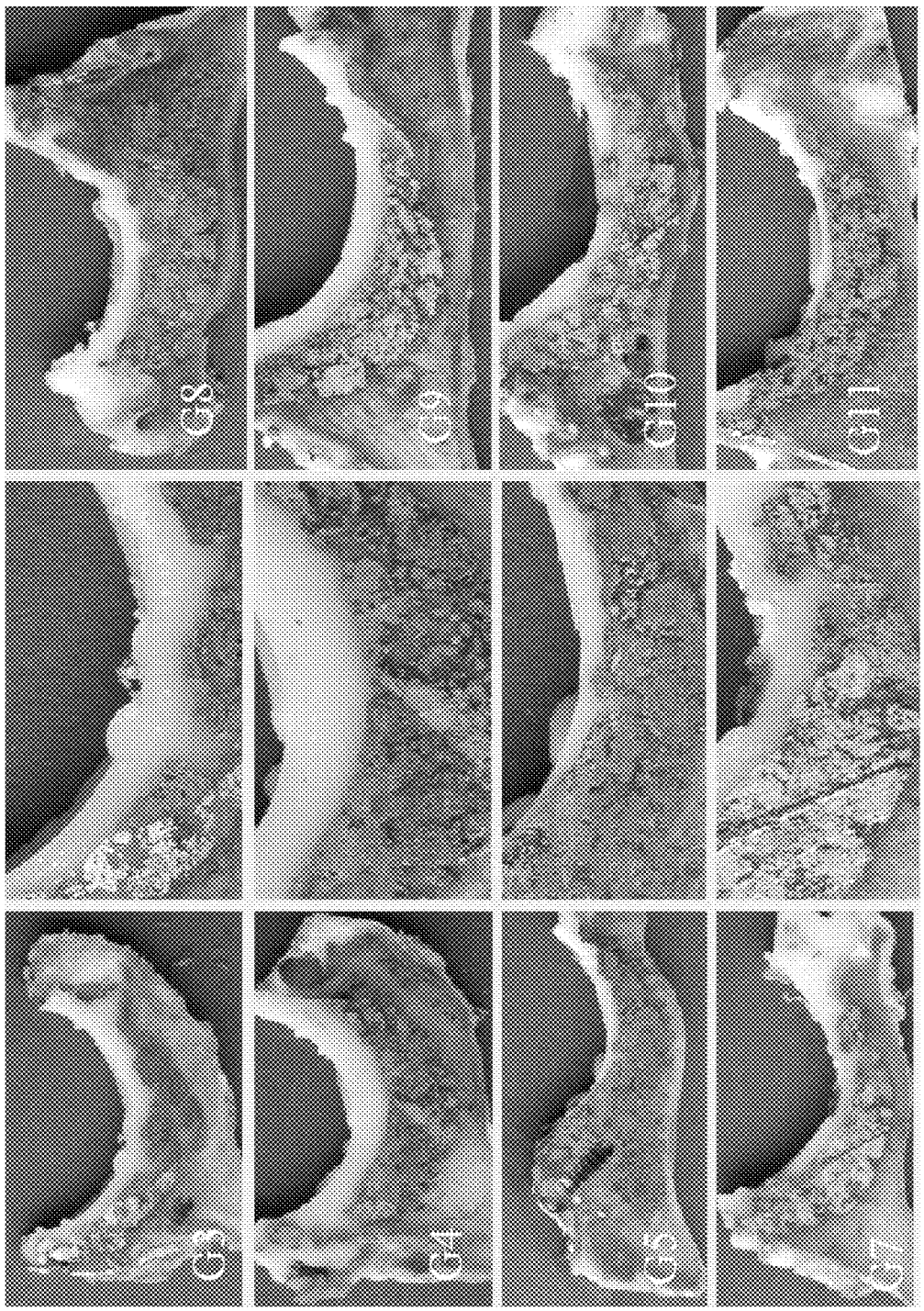
Figure 23:
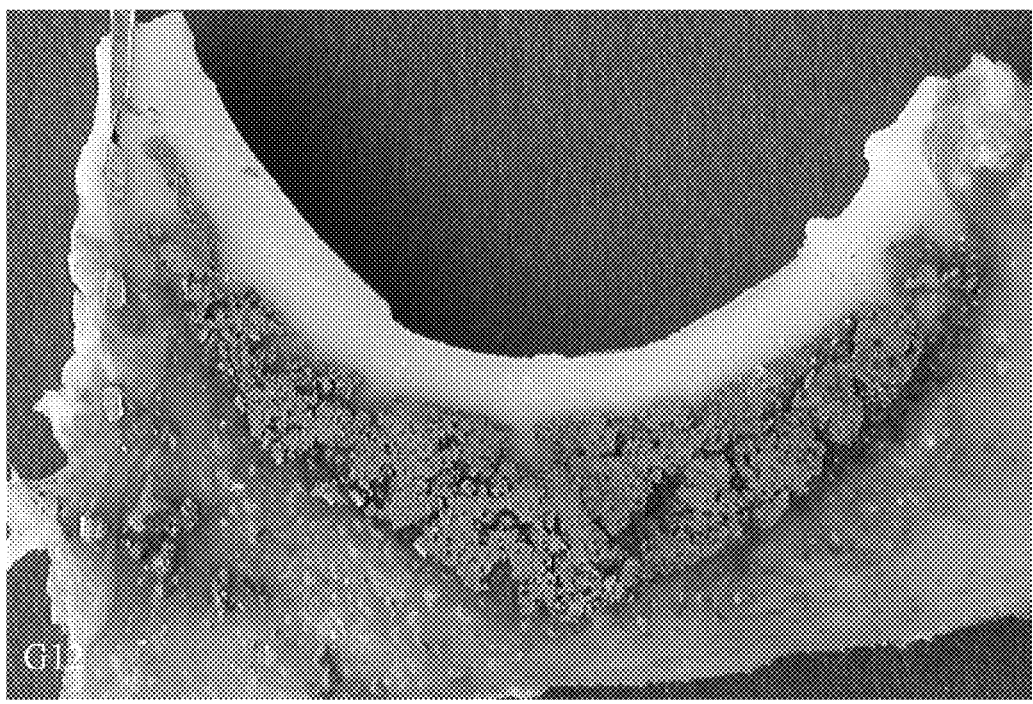
Figure 24:
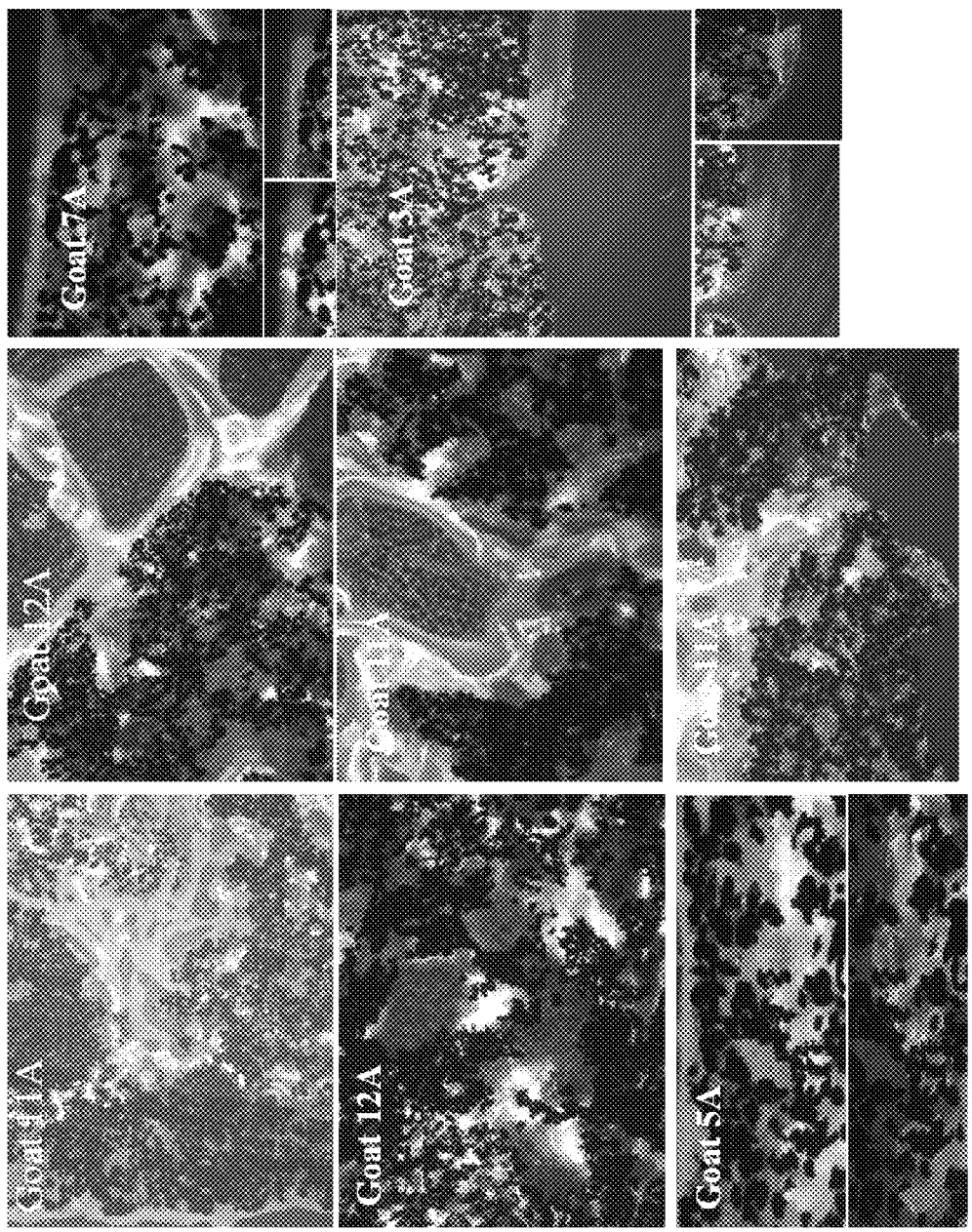
Figure 25:
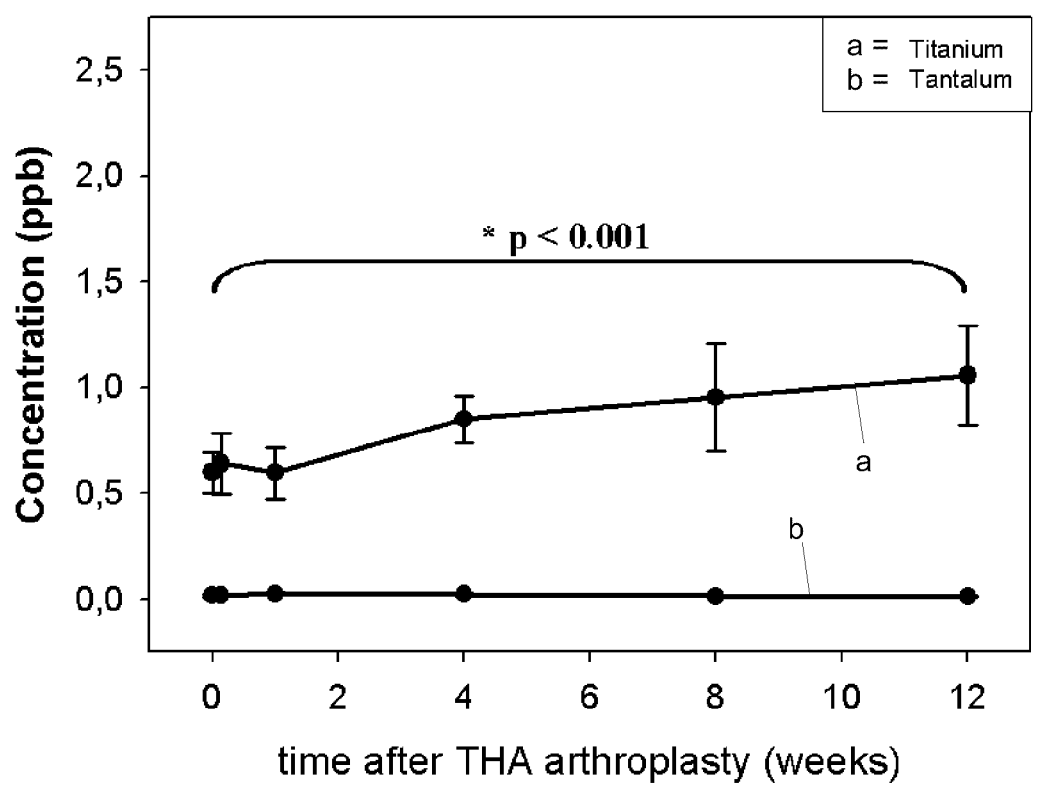

FIGS. 13A and B schematically an acetabulum component in a lever-out testing equipment and the fixation of said component in said testing equipment;

FIG. 13C schematically an acetabulum component in cross section;

FIG. 14 shows an acetabulum component loaded by a ball joint;

FIGS. 14A and B a diagram of the displacement and rotation of each group and a diagram showing lever out moments (Nm) for acetabulum components in testing equipment according to FIG. 13, using four different materials;

FIG. 14C a diagram of cement penetration;

FIG. 15 in cross section a photograph of an acetabulum component, showing the average cement penetration;

FIG. 16 in cross section schematically a bone conduction chamber used for evaluating bone ingrowth;

FIG. 17 a cross section of a graft cylinder of impacted Ti granules;

FIG. 18 a diagram showing bone ingrowth in mm of different graft groups;

FIG. 19 a photograph of a porous mass of Ti-particles, fibrous tissue and lacunes of osteocytes and mineralized bone matrix, showing direct contact between bone and titanium;

FIG. 20 a photograph of a cross section of a filled defect, showing the in growth of bone tissue into the filling porous mass and a diagram of the in growth distance for different grafts filling said defects;

FIG. 21 a typical section through the implant;

FIG. 22 a cross sections through the implant of goats 3, 4, 5, 7, 8, 9, 10, 11. Notice variable cement thicknesses. Integration of TiP layer with host bone always good. Interfaces of TiP layer with cement always absent or very thin (<100 micron);

FIG. 23 a larger magnification of reconstruction of goat 12;

FIG. 24 a detail of Larger magnifications of details of bone ingrowths and TiP cement interfaces;

FIG. 25 a Ti levels during the experiment.

The present invention will be elucidated with reference to the examples, wherein a femoral hip prosthesis, especially a total hip revision or at least a revision at the acetabular side or at the femoral side is described by way of example. The same and similar techniques and materials can also be used for other prosthesis fixations and filling of osseous defects. The invention is not limited to the embodiments shown. Variations and combinations of parts thereof are considered to be disclosed also.

In this description host is at least a human or animal body or part thereof, either natural or artificial, to which a prosthesis is fixed and/or in which an osseous defect is filled. Graft material is at least material that is at least partly solid and is used for filling voids and fixating a prosthesis or parts thereof, including autografts, allografts and/or xenografts. Impacting includes at least applying an impact force such as but not limited to hammering. Bone cement includes but is not limited to liquid or paste which is settable and adheres to different filling materials for the acetabulum or femur, which could be for instance bone or host tissue and/or to metal, ceramics and/or plastics used for prosthesis or parts thereof.

In a method or kit of parts according to the invention granules can be used, having a porous structure, made of metal, in particular titanium based such as pure titanium or a titanium alloy. The porosity is preferably such that open channels or labyrinths extend throughout the entire granule. The granules may be made by a chemical reaction of titanium and titanium tetrachloride (TiCl4), during purification. The TiCly chemical reaction can be induced with for example magnesium or Natrium. Using natrium can have the advantage that the porosity of the granules can be mechanically advantageous.

The granules can have a high purity, such as 99%. Titanium or more. In one embodiment the purity can be 99.8% or more. In another embodiment the purity can be 99.9% or more.

The granules may be coated, for example using any osteoconductive or any osteoinductive coating, for instance comprising calcium phosphate. The coating can also partly or totally consist of agents that have an effect on bone growth or by addition of drugs or other substances like for instance a chemotherapeuticum, depending on the application of the granules. The granules are non-degradable and bio compatible. The granules can have a relatively rough surface and can be relatively large, compared to the granules used in a method as described in WO 00/13615. In an advantageous embodiment the granules cling together as a result of their surface structure and roughness.

The granules may be soaked in a fluid prior to use, filling at least part of the porosities in and/or between granules and providing an adhering force between the granules. The granules can be compacted outside an opening in a bone, but are preferably compacted such that the adhere to each other, inside an opening in a bone in which a prosthesis has to be fixed and/or which forms an osseous defect and/or comprises an osseous defect. The fluid can have an effect on the porosity, increasing the porosity of a compacted amount of granules. The fluid can have the effect of reducing the compaction. The fluid can have the effect of making the granules cling together better then when dry, especially also before compacting. The fluid can have the effect that the granules in wet state cling less to human or animal tissue, especially soft tissue such as flesh, muscles and tendons, around an opening for fixating a prosthesis or part thereof, resulting in the effect that such granules can be more easily removed then when dry. The fluid can have the effect of limiting cement penetration between and in granules.

Granules according to the invention can be compacted by impact force applied to the granules, for example when loosely poured into a container such as a mould or, in an advantageous embodiment, into a hole in a bone in which a prosthesis or part thereof is to be fixated. Surprisingly granules made of porous metal such as titanium or a titanium alloy were far more impactable than BoP or CeP, assessed as impaction strain after a standardised impaction. Moreover, after impaction, granules were subjected to a compressive force that is comparable to compressive forces in an artificial hip joint (2.5 MPa). After compression, TiP showed less deformation than CeP, and less deformation than BoP. After compression, granules were allowed to relaxate. During relaxation TiP recoiled farther, compared to the deformation that was caused by the compressive force, than BoP and CeP particles compacted with the same impacting force. After impaction the metal granules showed only limited further plastic deformation in vivo, resulting in a very stable fixation. The granules may be vibrated prior to impaction, for increasing the density.

Granules used in the present invention may show, under in vivo loading conditions and after impacting, limited further plastic deformation. The porosity may be such that fixation and strength of the graft layer can be increased by in-growth of host tissue. Porous metal granules impacted according to the invention may have mechanical flexibility which is larger that the mechanical flexibility of ceramic particles impacted in the same manner. Highly porous metal granules can have an internal porosity of more than 75%, preferably more than 80% and according to the invention can have interconnected pores. When impacted according to the present invention the resulting material can result in a stable material, which may be referred to as a cookie, at least when made outside the human or animal body. Such material will have inter-granule porosity, which is formed by pores between granules, and internal porosity, which is formed by pores within said granules. Granules for use in the present invention preferably are made of or contain titanium or a titanium alloy, which is known to be bio-compatible and allow direct implant-to-bone contact and can have a fixation strength to host tissue which is superior to stainless steel.

Experiments

In vitro and in vivo experiments were conducted using porous titanium particles (TiP) according to the present invention. As reference materials ceramic particles (CeP, BoneSave®, Stryker Howmedica Osteonics, Limerick, Ireland) and morsellized human cancellous bone particles (BoP) as shown in FIGS. 9 and 10.

Figure 9A:
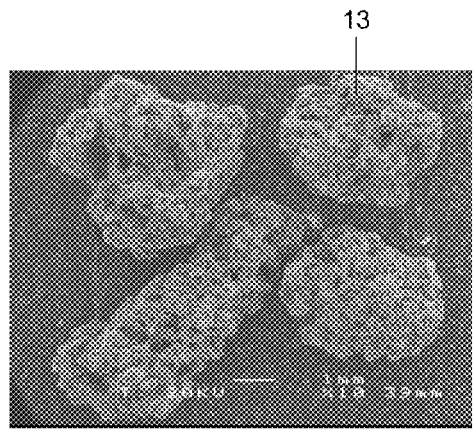
Figure 9C:
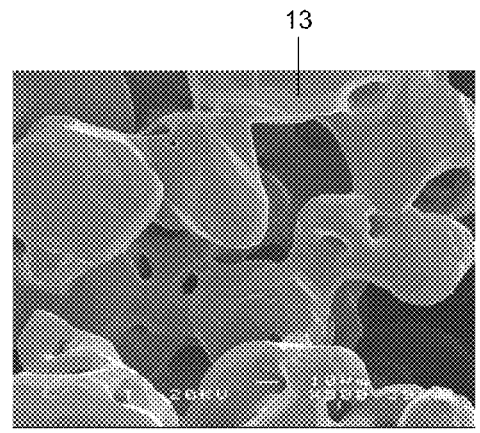
Figure 9B:
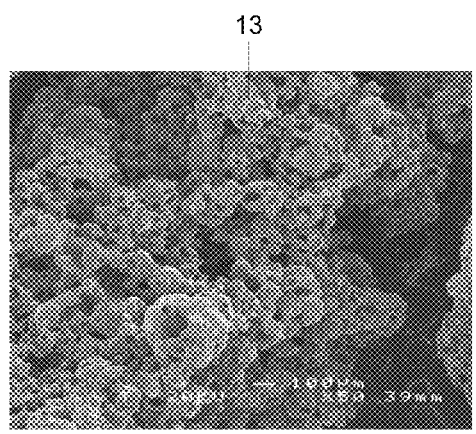
Figure 9D:
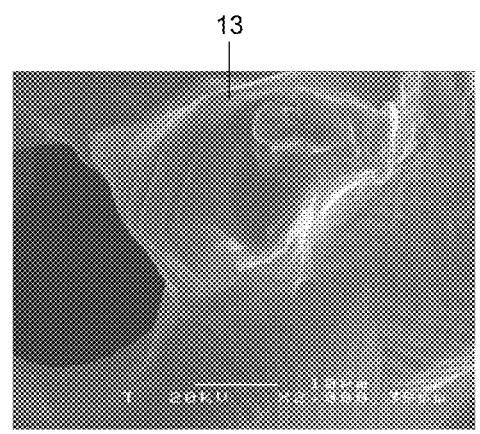

The porous titanium particles as used were produced during the purification of titanium through titanium tetrachloride ($TiCl_4$) and Na. This process creates a crystalline microtexture (FIG. 9D). The granules used had a diameter in the range of 3.0-5.0 mm (they passed a 5.0 mm pore sieve, but were stopped by a 3.0 mm pore sieve). From cross-sectional photographs (SEM, Jeol 6310 scanning electron microscope) the porosity of the cross sectional surface of TiP was calculated to be approximately 83%, titanium forming approximately 17%. Pores are interconnected.

BoneSave® is a commercially available bioceramic that is constituted of 80% TCP and 20% HA and with a non interconnective porosity of 50%. CeP used in this study had a diameter of about 2.0-4.0 mm.

Morsellized cancellous bone chips (BoP) were obtained by nibbling the cancellous bone of five freshly frozen (−80° C.) human femoral heads with a rongeur. Large bone chips (about 7×10 mm, ellipsoid shape) as recommended by Bolder et al and Dunlop et al. Bone grafts were not rinsed before testing and were adapted to a temperature of 30° C. TiP and CeP were soaked in water during thirty minutes before impaction. All particles were tested at room temperature.

Specimens 107 of BoP contained 4.0 grams of particles, specimens 107 of TiP and CeP contained 3.0 respectively 4.0 grams of dry particles. Particles were impacted in a cylindrical brass testchamber 100 with a diameter of 20.5 mm. A specially designed impactor 101 was used, as shown in FIG. 11, for standardized impaction of the grafts. The diameter of the impactor 101 was only slightly smaller than the diameter of the test chamber. To allow for free removal of fat and fluid out of the grafts and the test chamber 100 during impaction, three release channels 102 with a diameter of 2.0 mm were made to the side of the impactor 101. All specimens were impacted by dropping a weight of 420 grams onto the impactor thirty times from a height of 35 centimeters. This results in a degree of impaction of bonegrafts similar to impaction in a sawbone acetabulum by an experienced orthopaedic surgeon (BWS). Height before impaction and after impaction was measured with a marking gauge (resolution 0.05 mm). To determine the impactability of the materials the impaction strain was calculated. Height of the specimen before impaction was indicated by $h_{init}$, height directly after impaction and at the beginning of loading was indicated by $h_0$. The impaction strain was calculated as:

$$\epsilon_{impaction} = [\ln(h_{init}/h_0)]$$

Directly after impaction the resulting graft layer was loaded in the same testchamber 100 with a confined compression test (CCT). To judge the interparticle entanglement desired for an adequate reconstructive behaviour, some extra specimens 107 were impacted. These specimens 107 were not used for mechanical testing and were removed from the test chamber 100 for macroscopical evaluation directly after impaction. Such specimens 107 in the form of cookies are shown in FIG. 10.

The CCT was used previously to measure the time-dependent mechanical properties of bone grafts, different bioceramic particles and mixes of bone grafts and bioceramic particles after manual impaction (Verdonschot N, van Hal C T, Schreurs B W, Buma P, Huiskes R, Slooff T J. *Time-dependent mechanical properties of HA/TCP particles in relation to morsellized bone grafts for use in impaction grafting. J Biomed Mater Res.* 2001; 58(5):599-604) In this study the CCT was used to measure the deformation and stiffness of the graft layer during loading, and the visco-elastic recoil of the graft layer during subsequent unloading (relaxation). After impaction, a frame was placed on top of the test chamber 100 with a rigid porous filter 105 on top of the specimen to allow free fluid exudation during loading. On top of the filter 105 a load spreader 106 was placed to ensure that the applied load was equally distributed over the whole surface of the specimen 107. The specimen 107 was subjected to cyclic loading (0.1-2.5 MPa (20-840 N)), at a frequency of 1 Hz during 900 seconds while measuring deformation and stiffness of the graft specimen 107. The applied loading corresponds with stress levels that may be expected around cemented implants and was applied by a servo-hydraulic MTS machine (MTS® Systems Corporation, Minnesota, US). An extensometer 108, connected between the loading rod 109 and the specimen 107, measured the height of the specimen 107 during the test. Using a load cell 109 placed under the chamber 100 the applied load was registered (FIGS. 11 and 12).

The loading strain represents the deformation of the materials under dynamic loading. Bone grafts show creep behavior: the specimen 107 height diminishes during the loading period. During every loading cycle the height of the specimens was recorded at minimum stress ($h_{minimum\ stress}$, height at 0.1 MPa) and at maximum stress ($h_{maximum\ stress}$, height at 2.5 MPa). The loading strain was calculated as:

$$\epsilon_{loading} = [\ln(h_{minimal\ stress}/h_0)]$$

The loading strain was determined for every loading cycle and statistically compared for the values obtained at the end of the loading phase. After 900 seconds of loading the specimen 107 was allowed to relaxate (0 N load) during 900 seconds to measure the visco-elastic recoil.

The cyclic elastic modulus represents the stiffness of a material. The elastic modulus is calculated from the change in stress within one loading cycle (cyclic stress) and the corresponding resulting deformation within the same loading cycle (cyclic strain). The cyclic stress, σ cyclic, was calculated as the difference between minimum stress (0.1 MPa) and maximum stress (2.5 MPa) and remained constant for every loading cycle (2.4 MPa).

The cyclic strain, ε cyclic, was calculated as:

$$\epsilon_{cyclic} = [h_{minimal\ stress} - h_{maximum\ stress}]/[h_{minimal\ stress}]$$

The cyclic elastic modulus, E, was calculated as the ratio of the cyclic stress and cyclic strain:

$$E = [\sigma_{cyclic}/\epsilon_{cyclic}]$$

Because the cyclic stress was constant, the stiffness was inversely proportional to the cyclic deformation. The stiffness was determined during the whole loading period and statistically compared for the values obtained at the end of the loading phase.

Soaked TiP and CeP were poured in the test chamber. The water film made the unimpacted TiP and CeP stick together quite well. Standardized impaction of used graft amounts resulted in graft specimens with comparable initial height (range 14.5-16.9 mm, table 1 (mm)). TiP and CeP were more impactable than BoP (FIG. 10, table 2). In table 1 and 2 the standard deviation is given between parentheses. Considerable water was released from TiP through the side channels of the impactor. A smaller extent of water, which had a milky appearance and contained a lot of minute ceramic granules, was released from CeP specimens, which in vivo can be a hazard to the health of the host. BoP released a lot of fat during impaction.

TABLE 1 height of graft specimens

| graft material | initial | after impaction | after loading | end of test |
|---|---|---|---|---|
| TiP | 16.49 (0.31) | 7.53 (0.21) | 7.46 (0.21) | 7.53 (0.21) |
| CeP | 14.67 (0.24) | 6.89 (0.14) | 6.77 (0.15) | 6.83 (0.14) |

TABLE 1-continued height of graft specimens

| graft material | initial | after impaction | after loading | end of test |
|---|---|---|---|---|
| BoP | 15.65 (0.58) | 9.78 (0.37) | 7.35 (0.55) | 8.13 (0.50) | table 1

TABLE 2 mechanical parameters of graft specimens

| graft material | impaction strain | loading strain | relaxation strain | stiffness (MPa) |
|---|---|---|---|---|
| TiP | 0.78 (0.03) * | 0.009 (0.001) * | 0.009 (0.001) * | 209 (20) * |
| CeP | 0.76 (0.02) *] | 0.017 (0.002) *] | 0.009 (0.002) *] | 334 (47) *] |
| BoP | 0.47 (0.01) | 0.29 (0.05) | 0.10 (0.02) | 80 (18) |

After impaction, TiP formed a unified cylinder which maintained nicely it's shape. The firm entanglement of impacted TiP created homogeneous macroporous 'cookies' 107 which were very cohesive and could not be broken easily. Impacted specimens of BoP were less cohesive than specimens of TiP but stuck together after removal from the test chamber. Impacted CeP specimens tended to disintegrate after removal from the impaction chamber and fell apart quite easily.

Mechanical Testing: Loading and Relaxation

TiP cookies 107 showed almost no deformation during physiological loading. At the end of the loading phase TiP specimens showed a strain of 0.009±0.001 (table 2). CeP deformed twice as much as TiP (loading strain 0.017±0.002). Compared to these synthetic grafts, BoP deformed considerably more and showed a loading strain of 0.29±0.05. This was significantly more than the other groups ($p<0.001$).

After a setting phase of about fifty loading cycles, stiffness remained almost unchanged during the rest of the loading period for all groups. There was a clear and significant difference between the three tested materials (table 2). TiP cookies 107 showed an intermediate stiffness (209±20 MPa) and were about 2.5 times as stiff as BoP cookies (80±18 MPa, $p<0.001$). CeP cookies were about 4 times as stiff as BoP cookies (334±47 MPa, $p<0.001$) and therefore stiffer than TiP cookies ($p<0.001$).

After unloading the TiP cookies 107 (FIG. 10B) showed no residual deformation: relaxation strain was equal to loading strain (0.009±0.001). For the CeP cookies 107 (FIG. 10D) only 50% of the loading strain recovered during the unloading phase (loading strain and relaxation strain 0.017±0.002 respectively 0.009±0.002). Although BoP specimens 107 (FIG. 10F) showed a large relaxation strain of 0.10±0.02, this was still only one third of the loading strain (0.29±0.05). The fat that was forced out during cyclic loading, was partially resorbed back into the bone grafts during relaxation. The visco-elastic behaviour of BoP cookies 107 during loading and subsequent relaxation is clearly apparent and shown in FIG. 12.

Porous titanium particles which are impactible and adapt to defect geometry are provided according to the invention as graft material for application in impaction grafting. Like calciumphosphate, porous titanium in bulk application is an osteoconductive material. It provides good bony anchorage after implantation which may be farther enhanced by roughening or by application of a bioceramic coating such as calcium phosphate.

Although constituted of pure metal, the compressibility of the highly porous titanium matrix of the granules 13 was impressive. Unimpacted TiP can often be visibly deformed by forceful compression between two fingers. TiP deformed even more than BoP during impaction and created a firmly entangled graft layer. The combination of high impactability and firm entanglement can be important for the application in impaction grafting: granules 13 stick together well after only slight impaction and can be impacted further easily. Porosity of the titanium 'cookies' remained as high as 70-75% which is also a positive feature as there is ample interparticle space for tissue in-growth. Porous titanium particles are very ductile, have more rounded edges than CeP particles after compacting and can be gradually compressed. This will prevent the occurrence of high contact stresses as seen during the application of CeP in impaction grafting.

A layer of impacted TiP according to the invention is highly resistant to both compression and shear stress and allows only for small plastic deformation after reconstruction and in-vivo loading. This leads to excellent primary stability, which is a prerequisite in orthopedic surgery for tissue and especially bone ingrowth. With the confined compression test the resistance against compressive stress was tested. Impacted TiP were very resistant to compressive forces. TiP have the surprising characteristic of combining impactability and stability after impaction. Deformation of TiP during loading was very small and completely reversible during subsequent relaxation. As opposed to the synthetic materials TiP and CeP, BoP showed a considerable amount of displacement during loading despite realistic impaction: during loading the impacted BoP specimens lost about 25-30% of their original height and only one third of this deformation was corrected during elastic recovery. From observations made of impacted specimens, it appears that a reconstructive layer made from the highly entangled, almost unified impacted TiP will be much more shear resistant than a similar reconstructive layer made of BoP or any mixture of BoP and CeP.

It is generally accepted that plastic deformation imposes a thread on vitalization of the graft layer and that. However, some elastic deformation as allowed by the granules according to the invention appears to be beneficial for tissue in-growth and incorporation. Limited Axial micro motions during loading stimulate incorporation and ossification of bone grafts. A high stiffness of the graft material such as CeP prevents these micro motions and could prevent osseous differentiation of in-growing tissue by stress shielding. Impacted TiP particles are about as stiff as a 50/50 weight mix of bone graft and BoneSave® (217±14 MPa). Acetabular reconstructions made with a similar graft/BoneSave® mix (50/50 volume mix) showed good graft incorporation. TiP provides for a suitable alternative for such mixture and has better elasticity and impactability.

In order to assess bone ingrowth after implantation holes were drilled in a bone in the knee area of a goat, which holes were filled with impacted TiP which was coated with a CaP (tricalcium phosphate/hydroxyapatite) coating with a mean thickness between 1 and 100 micrometer and impacted TiP without such coating respectively. Bone ingrowth was assessed after 4 weeks and after 12 weeks. The results are shown in table 3 below.

TABLE 3

|  | 4 weeks | 12 weeks |
|---|---|---|
| with coating | 3.0 mm | 3.2 mm |
| without coating | 0.6 mm | 2.0 mm |

From the test performed in vitro and visual inspections, compared to knowledge of the skilled person, it shows that the properties of TiP are superior to BoP and CeP in various aspects and that TiP is highly suitable for fixating prosthesis in human or animal bodies and for filling osseous defects.

Figure 1:
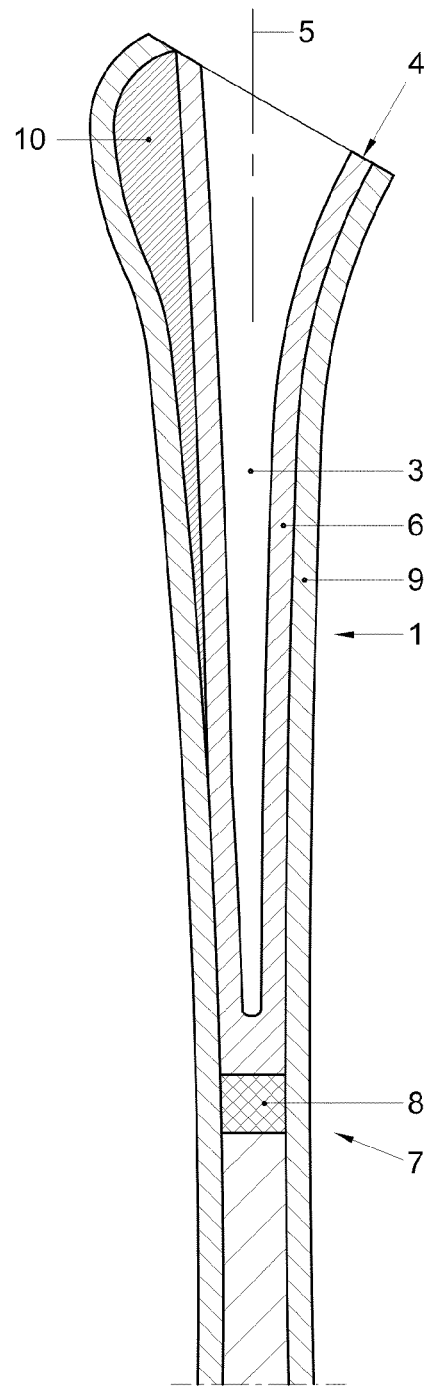
FIG. 1 shows schematically, in longitudinal section, a femur with an elongated opening from which a femoral component of a hip prosthesis has been removed.

In FIG. 1 a femur 1 is shown, in longitudinal section, of which the femoral head has been sawn off. In the embodiment shown in FIG. 1 a previously placed prosthesis or at least the femoral part 2 thereof has been removed, for revision surgery. The present invention can be related to total hip arthroplasty (THA) or other prosthesis surgery, both in first placements and in revision surgery. In FIG. 1 an elongated hole 3 is shown, extending from the saw-off plane 4 along a longitudinal axis 5 of the femur 1. A bone cement layer 6 extends along the inner surface of said hole 3, which is closed off at the distal end 7 by a plug 8. The bone cement layer 6 is the remaining part of the bone cement used for the now removed femoral component of the previously used prosthesis. If the present invention is used for a first placement the hole 3 can be drilled and/or reamed into said bone in a known fashion. The bone cement layer 6 abuts partly against cortical bone 9 and/or against spongeous bone 10.

Figure 2:
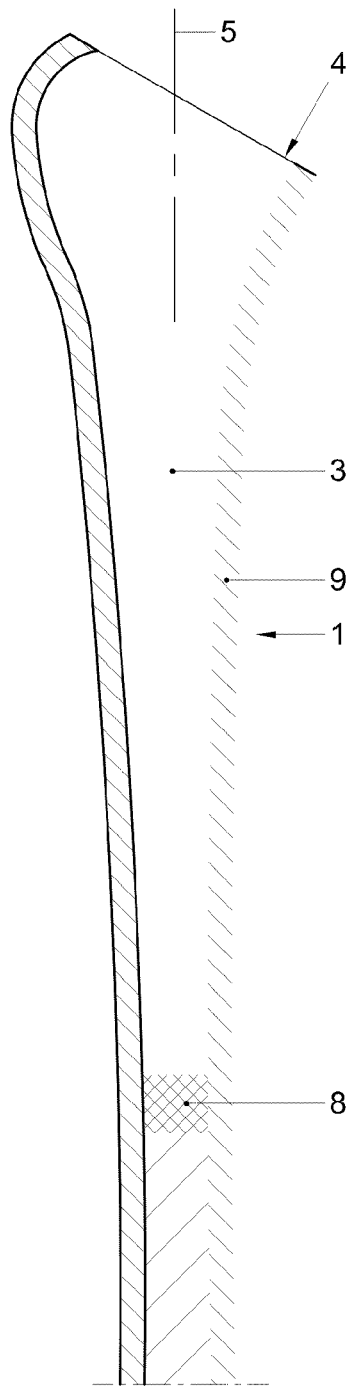
FIG. 2 shows schematically the femur according to FIG. 1, wherein the opening has been widened, by removal of for example a previous cement layer and/or bone, for example by reaming.

In FIG. 2 the cement is removed using appropriate tools such as a drill and/or reamer.

Figure 3:
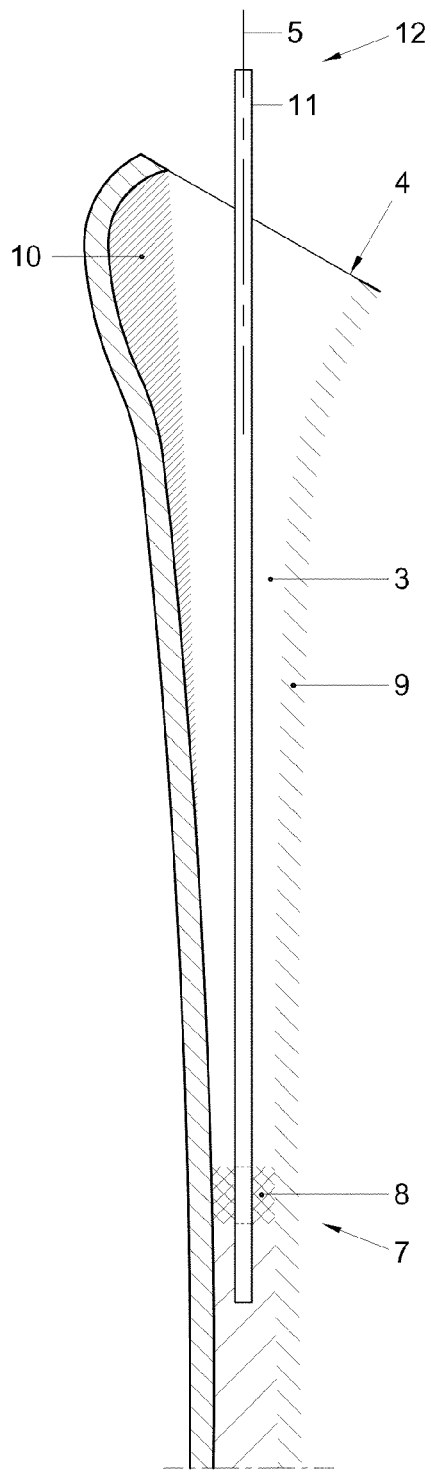
FIG. 3 shows schematically the femur according to FIG. 2, wherein a guide wire is positioned.

In FIG. 3, a guide wire 11 is driven into the plug 8, which guide wire 11 extends more or less parallel to the longitudinal axis 5 of the femur, from said plug 8 to a proximal end 12 outside said hole 3.

Figure 4:
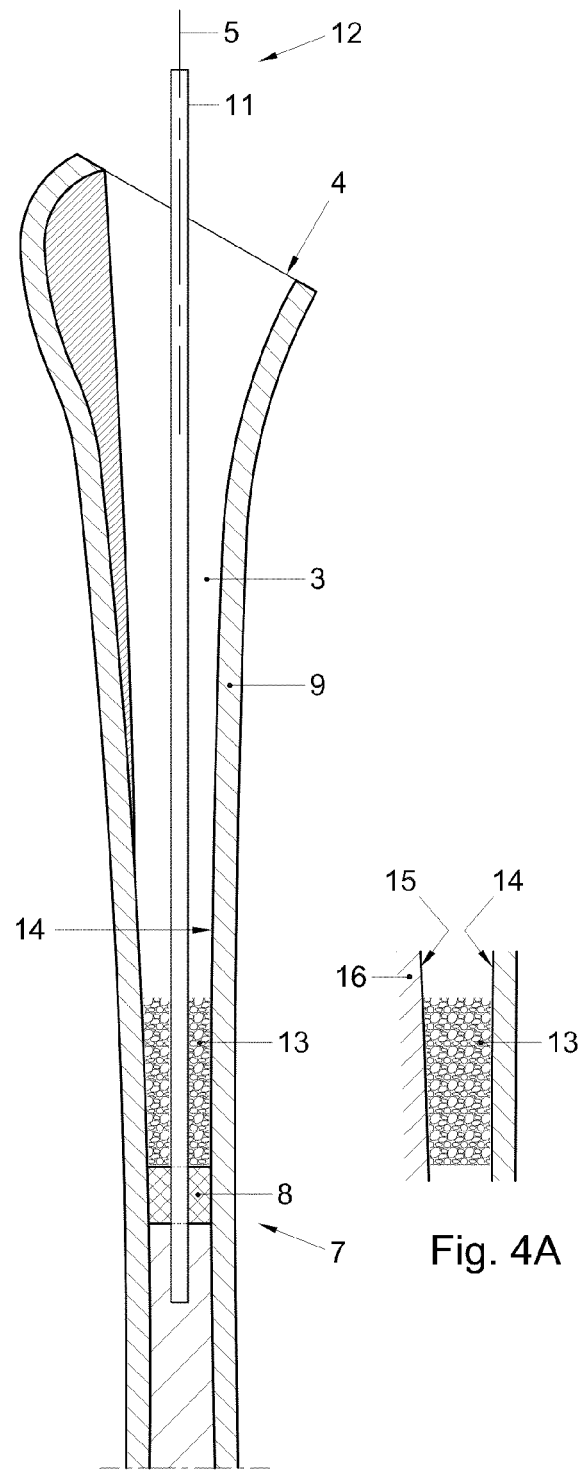
FIG. 4 shows schematically the femur according to FIG. 3, wherein the most distal part of the opening is partly filled with porous metal granules.

In FIG. 4 granules 13 are shown, deposited in the hole 3, resting against the inner wall or surface 14 thereof and against the plug 8, thereby prevented from penetrating in the spongeous bone, marrow or other parts of the host. The type of granules 13, which are porous having interconnected pores, in this embodiment made by purification of titanium by titanium tetrachloride (TiCL4), will be discussed in greater detail later. The granules 13 preferably have been soaked in a fluid, prior to introduction thereof into said hole 3, such that at least some of the fluid is adhered to the outer surface, which is relatively rough, whereas the pores thereof can be at least partly filled with said fluid. The fluid, for example a saline solution, has the advantage that the granules tend to stick together and are prevented from clinging to host tissue prior to impacting, as will be discussed. In FIG. 4A in an enlarged view a part of the granules 13 is shown, positioned between the inner surface 14 of the hole 3 and the outer surface 15 of a compacting device 16 as is shown in FIG. 5.

In FIG. 5 a compacting device 16 is guided over the guide wire 11 and has an outer shape 17 that largely corresponds to the shape of the femoral component 2 to be fixed in the femur 1. Such guiding is known from for example U.S. Pat. No. 5,047,035. In cross section perpendicular to a longitudinal axis 18 of said compacting device 16 the surface area of each cross section is slightly larger than the surface area of a corresponding cross section of the femoral component to be placed, such that when the contours of said cross sections are interposed, as schematically shown in FIG. 5A for one level, the contour of the compacting device extends around and spaced apart from the contour of the femoral component 3.

When the compacting device 16 is driven into the granules 13, as is shown in FIG. 5, the granules 13 are forced outward, in the direction of the inner surface 14 of the hole 3, and into each other. The force for driving the compacting device into the granules can be obtained by hammering, for example by hitting a proximal end 20 of the compacting device 16 with a hammer. The force exerted is an impact or impulse force, rather than a constant or smoothly increasing or decreasing pressure force. Due to the impact, the surface roughness of the granules 13 and their mechanical flexibility, the granules 13 will cling together strongly. If the granules 13 have been soaked in a fluid such as water, the inter porosity is relatively large compared to inter porosity of identical granules impacted without being soaked prior to impact. The difference can for example be in the range of 8 to 12%. The fluid is at least partly forced out of the granules or the layer of granules by said impact and/or will drain from the granules and is absorbed by the host.

The granules have a surface roughness sufficient for them to cling together. Preferably the surface roughness is over 5.5 Ra, more specifically over 6 Ra. Very good results could be obtained with granules having a surface roughness of over 6.3 Ra.

Preferably a layer 21 of granules 13, interconnected, is formed against most and preferably all of said inner wall 14 of the hole 3, having a thickness T of for example on average the equivalence of one to ten times the average size of the granules, as is shown in FIG. 6. Such layer 21 can be obtained by forming in a number of subsequent steps of filling the space between the inner wall 13 and the compacting device partly, impacting, and then repeating said step, until the entire layer 21 is formed. The granules used can for example have an average size between 1 and 10 mm, at least for 50% of the total volume thereof. They can have an average size of between 2.5 and 7 mm, more preferably between 2.5 and 5.0 mm. All of the granules can have a size within one of said ranges. The size of the granules is defined by sieving. For example granules in the range between 3 and 5 mm can pass through a 5 mm sieve but not through a three mm sieve. The granules 13 can be provided with a coating, for example a bio-compatible, host tissue in-growth enhancing coating. The granules can be coated with a coating containing or existing of calcium phosphate. A layer of coating on the granules can have a thickness of between 0.5 and 100 micrometer.

After providing the layer 21 of granules 13, which layer 21 is relatively form stable, the compacting device 16 and the guide wire 11 may be removed, leaving a void 22 above the plug 8, in which the stem 23 of a femoral component of a prosthesis can be positioned. Due to the difference in the sizes of the corresponding cross sections in the compacting device 16 and the stem 23 of the femoral component 2 of the prosthesis, said stem 23 can be positioned in said void 22 with a slight distance D between the inner surface defined by the layer of granules 13 and the outer surface of the stem 23, which forms a contact surface 24 of the femoral component 2. As is shown in FIG. 6 an amount of bone cement 25 is poured or injected or otherwise provided in said void 22, which amount is sufficient to fully cover the entire contact surface extending inside said void with a layer that is thicker than the said distance D between the granules 13 and the contact surface 24. The cement can be put under pressure before forcing the stem into the cement. When the stem 23 is forced into the void 22, as is shown in FIG. 7, the bone cement 25 is forced up along the contact surface 24 as well as partly into the pores between the granules 13, filling the inter porosity. A small part of the bone cement might also enter pores of granules 13. In FIG. 7A on an enlarged scale part of the inner surface 14 and stem 23 are shown with the layer of granules 13 in between. As is shown the thickness Dg of the layer 22 of granules 13 is smaller than the width W of the gap 26 between the inner wall 14 and the stem 23, the rest of said gap 26, which has a width Dc being filled with a layer 27 of bone cement, which extends over a distance Dp into said layer 22 of granules. The distance Dc is preferably is between 1 and 4 times the average diameter of the granules, wherein the thickness of the cement layer is preferably at least approximately 2 mm in average, in order to prevent mechanical failure, and the cement preferably penetrates the layer of granules over a distance on average of approximately 2-x mm, wherein x represents the diameter of the largest granule used in the specific reconstruction. The thickness of the cement layer preferably is approximately constant over the contact surface of the prosthesis, such as the outer surface of a prosthesis fixation part such as a femoral stem or the outer surface of an acetabulum component, but may vary.

In a method and prosthesis fixation according to the present invention initial fixation of the prosthesis is mainly or at least to a large extend obtained by the granules being interconnected and compressed to the inner wall 13 of the hole 3 in the host femur or other surface, and the bone cement 25 adhering to the granules 13 and to the contact surface 24 of the prosthesis. The granules having a relatively rough surface will inter alia mechanically cling together when compressed against each other. The layer 22 of granules 13 proved to have a high resistance to compression and probably to shear stress, whereas it allows small plastic deformation only after (reconstructive) surgery, during in vivo loading. This leads to a very high stability without the risk of lasting deformation of the layer 22, resulting in high stability of the prosthesis fixation and reduced risk of fractures. The limited plastic deformation appears to improve bone and other host tissue in-growth. This may be the result of inter alia axial micro motions during loading, which could stimulate ossification of bone grafts, whereas the granules allow transduction of loading to in-growing tissue, due to the flexibility.

For performing a prosthesis surgery or filling operation according to the invention a kit can be used comprising at least a prosthesis and/or a mesh, porous granules having interconnected pores and bone cement, as well as an impacting device for impacting and compacting a layer of said granules. The granules may be coated and may be soaked. The impacting device, which can also be referred to as compacting device, can comprise at least a stem part 23, which may consist of parts that can be used individually or in combination with each other. The stem preferably tapers slightly in the direction of a distal end, directed during used towards a side facing away from an impacting face, for forcing outward said granules. The kit can further comprise a plug with guide wire. Various compacting devices can be provided, for subsequent use, each following compacting device having for example a slightly larger cross section then the compacting device used in the previous step. The kit preferably comprises sufficient granules to cover a contact surface of the prosthesis or part thereof in the kit with a full layer of granules having a thickness at least one granule and preferably at least three granules. Furthermore it is advantageous when the amount of bone cement in the kit is sufficient to cover said layer of granules with a full layer of bone cement having a thickness comparable to the thickness of the layer of granules.

Prior to placement of the femoral stem the bone cement may to a very large extend or even completely fill the volume of the opening into which the stem is to be positioned. Upon positioning of the stem the cement will be pressurized inside said opening and the excess cement will be forced out at the proximal end. At an acetabulum component the entire opening of the acetabulum can be filled with cement, the excess cement being driven out upon placement of an acetabulum cup. The excess cement can then easily be removed. By way of example, which should not be explained limiting, for a THA (femoral and acetabular components) in a fully grown human being a quantity of about 75 grams of TiP (dry weight) with a porosity of 85-90% will have to be used.

The granules 13 preferably have a rough surface, such that granules poured loosely into a container will cling or adhere to each other mainly by surface particles of adjacent granules interconnecting. Granules made of ceramic material tend to break upon impacting, resulting in a poor stability and in small ceramic particles and debris which can roam freely, even into the surrounding host tissue, which can lead to health hazards. Porous metal granules according to the present invention prove to provide a more stable fixation than a similar use of BoP.

A realistic in-vivo THA was performed on three goats, using a method according to the present invention, as further elucidated by way of example with reference to FIG. 1-7, in which both the femoral and acetabular parts were replaced (total hip arthroplastic; THA) The goat weighed about 65 kg and 5-10 grams of TiP was used (dry weight) for fixation of the acetabulum. Directly after the operation the goat was placed in a hammock for ten days. From ten days after the operation the goats were allowed to load the prosthesis. After two weeks a level of titanium in the blood was measured below 10 ppb, which then decreased below 7 ppb, which is comparable to the concentration in a human being having a conventional well functioning Ti prosthesis. The TiP formed a stable reconstruction directly after the operation, which stability was maintained during three months after the operation. After three months the goat was euthanized and the prosthesis was visually inspected. Histology showed no signs of irritation, inflammation or foreign body reaction due to TiP, showing bio-compatibility. The prosthesis was fixated very good both by in-growth of fibrous tissue and bone tissue. Over the entire surface of the layer 22 of granules 13 in-growth of tissue and/or bone appeared, whereas there was direct contact between the metal of the granules 13 and the bone grown into the layer 22. At several positions there was no contact between bone and granules, but there an interface was formed by said fibrous tissue.

In FIG. 8 the filling of an osseous defect 28 is shown, using particles 13 which are impacted prior to and/or during placement in said defect 28, for example a cavity 29 formed during removal of the old bone cement or resulting from bone resorption, removal of a tumor or other grounds. The granules 13 or a cookie 107 formed thereof can be enclosed in said defect 28 by means of a mesh 30 which closes off the cavity 29 but allows bone and/or tissue to grow through the mesh into the granules and/or bone cement to penetrate at least interporosity of the layer 22 of granules 13. Thus relatively large cavities 29 can be filled and the anchorage of the filler can be obtained relatively easy, quick and firmly.

Acetabulum Components Experiment

FIG. 13A shows schematically a testing equipment 31, in which an acetabulum component 32 is positioned. A synthetic acetabulum model (Sawbones®) was used. FIGS. 13B and 13C show said acetabulum component 32, which is e.g. a plastic such as polyethylene semi spherical cup, fixed in a hollow, semi spherical chamber 33 of the testing equipment 31 representing the acetabulum and having a radius of approximately 30 mm, using a layer of Titanium granules 13 and bone cement 6. The granules 13 were poured in wet condition and impacted in said chamber 33, using a semi spherical compacting device 34 and a hammer, such that a hollow 34 was obtained having a radius of approximately 22.5 mm. The thickness of the layer of granules 13 was between 4 and 10 mm. The volume of the granules after impacting was about 55% of the volume prior to impacting. A cup 35 having a diameter of 42 mm was cemented into said hollow 34. Four groups of grafting materials were used, each in eight such testing devices 31, resulting in 32 testing devices.

Reconstructions were made with donor bone (I), donor bone mixed with Ti granules (II), Ti granules having a diameter between 3 and 5 mm (III) and Ti granules having a diameter between 4 and 7 mm (IV). All were used in the same testing device, using the same cement and the same dimensions. For using donor bone the instrumentation of Stryker was used. In reconstructions of group I 47.5 grams of donor bone was used, in group II 30 grams of Ti and 15 grams of donor bone was used, in group III and IV 37.5 grams of Ti granules was used.

After a minimum of 48 hours after cementing the reconstruction was loaded and the displacement of the cup 32 relative to the chamber 33 (acetabulum) due to loading was measured. The load was transferred to the cup 32 by using a spherical ball 35 as shown in FIG. 14, fitting exactly in said cup (diameter of 28 mm) which was subjected to 900 loading cycles of 2-3000 N) having a frequency of 1 Hz and was applied by a servo-hydraulic MTS machine 35A (MTS® Systems Corporation, Minnesota, US). The position before and after said loading cycles was measured at a static load of 3000N and were compared. The displacement and rotation was measured in X, Y and Z direction and measured as (displ=displacement; rot=rotatie):

Displacement: $[(displX)^2+(displY)^2+(displZ)^2]^{0.5}$

Rotation: $[(rotX)^2+(rotY)^2+(rotZ)^2]^{0.5}$

In FIG. 14A two diagrams are shown. The top diagram discloses displacement, the lower rotation for each of the groups I(B), II(TB), III(T3-5) and IV(T 4-7). These show that Ti provided the smallest displacement and rotation, although less grams are necessary wherein the smaller granules show the least displacement and rotation. The error beam shows the standard deviation within each group, smallest in the group III, the smallest granules.

After measurement of the displacement and rotation the sphere was removed and a beam 36 was fixed in the cup 32 by screws as shown in FIG. 13B. Near the free end 37 of said beam 36 a wire 38 was fixed having a length direction substantially perpendicular to said beam 36 in a starting position as shown in FIG. 13A. The wire 38 was retracted with a constant speed, the force F necessary was measured constantly over a trajectory of 10 cm. The maximum force $F_{max}$ over said trajectory was defined and multiplied with the distance between the point of connection of the wire 38 to the beam 36 and the point of rotation of the cup 32, which was approximately 14 cm. This was defined as the lever-out-moment (LOM) In this test each of the test construction of groups I and II failed in the sense that the cup 32 was levered out of the acetabulum. Of group III three constructions failed, in group IV only two. In FIG. 14B the LOM of each group is shown, the error beam showing the standard deviation. The Ti granule groups clearly were superior to the bone graft groups I and II.

In a further test penetration of bone cement into the layer of granules 13 was measured. From in vivo tests is has shown that cement penetration should be limited to a shallow depth in order to allow bone and other tissue to grow into said layer of granules. The penetration was measured by sawing a cup with the layer of granules in half along a mid section, as shown in FIG. 15. A semi circle 39 was positioned along the outer surface of the cup 32, which was then divided into 49 sections of an 1.8 degree angle. In each section the distance from said semi circle 39 to the penultimate point of the cement layer 25 was measured in radial direction through said section. In FIG. 14C for each group I-IV the average penetration depth (left hand column; Sum of all penetration depths divided by 49) and the average variation of penetration (right hand column) is shown, wherein the error beams show the standard deviation. The penetration into Ti particle layers can be preferable over bone graft layers.

Bone Ingrowth Experiments in BCC

In FIG. 16 schematically a bone compaction chamber 40 (BCC; Aspenberg) is shown, which basically comprises two pure titanium half cylinders 41, 42, held together by a hexagonal cap 43 screwed over said halves. The two half cylinders 41, 42 together form a pointy tip 44 and external screw thread 45 for screwing the BCC tip 44 first into bone B of a test bone, for example of an animal. Two openings 46 radially opposite each other and near said tip are provided for allowing growth of tissue into said chamber 40 from the surrounding, as is shown by arrows 47. In experiments performed BCC were implanted in the proximal tibia of goats. The in growth openings 46 were positioned at the level of the endostium by adjusting the cap 43 which was kept outside the tibia 48.

Materials and Methods

Six groups of BCC's were implanted: five groups filled with graft material and one empty control group (E). The five different graft materials consisted of four groups of porous titanium particles (TiP, Hereford Metal Powder Company Ltd, Hereford, UK) and one of impacted morsellized cancellous allograft bone particles (BoP) (Table 5 and 6).

TABLE 5

| group | graft material | volume fraction (%) |
|---|---|---|
| E | — | — |
| B | impacted cancellous allograft BoP | 61 ± 9 |
| T | TiP. not coated, not impacted | 22 ± 5 |
| Ti | TiP not coated, impacted | 44 ± 2 |
| Tc | TiP. coated, not impacted | 21 ± 5 |
| Tci | TiP. coated, impacted | 40 ± 5 |

TABLE 6

| graft group | available for analysis | bone ingrowth distance | p value |
|---|---|---|---|
| E | 20 | 3.6 ± 2.0 | <0.001 |
| B | 18 | 2.0 ± 1.0 | — |
| T | 22 | 0.9 ± 1.0 | 0.12 |
| Ti | 22 | 0.6 ± 1.3 | 0.001 |
| Tc | 22 | 0.9 ± 0.9 | 0.02 |
| Tci | 22 | 0.8 ± 0.9 | 0.01 |

A pool of cancellous allografts was obtained from freshly frozen (−40° C.) sternums of five goats that were nibbled with a rongeur to chips of about 1×2×2 mm after negative microbial culturing.

TiP were rather spherical particles with a diameter of 1.0-1.4 mm that were constituted of commercially pure titanium and had pores ranging 10-150 μm. Backscatter scanning electron microscopy imaging (BEI, Jeol 6310, Jeol, Tokyo, Japan) and interactive computer controlled image analysis (AnalySIS®, Soft Imaging System GmbH, Munster, Germany) were used to determine the titanium volume fraction of individual particles, by determining the cross sectional porosity. TiP were cleaned ultrasonically with 10% Extran® MA01 (Merck KGaA., Darmstadt, Germany), 1 M HNO$_3$, acetone and alcohol. In between these steps TiP were flushed and cleaned ultrasonically with demineralized water.

The coating of TiP consisted of silicium dioxide containing calciumphosphate (HA:TCP 60:40) and was applied by DOT (BONITmatrix®, DOT GmbH, Rostock, Germany). Physicochemical analysis of TiP and coated TiP was performed with X-ray diffraction (XRD, with a thin-film Philips X-ray diffractometer, using Cu Kα-radiation (PW3710, 30 kV, 40 mA)) and with a scanning electron microscope (SEM, Jeol 6310, Jeol, Tokyo, Japan) which was equipped with an energy disperse X-ray detector (EDS). TiP showed a crystalline smooth surface before coating. After coating TiP were covered with dense ceramic granules with a mean diameter of about 5 μm. Coating increased the weight of TiP by 3.5%. XRD showed that the BONITmatrix® coating contained biphasic calciumphosphate (HA/TCP 60:40). EDS revealed the presence of calcium, phosphate, silicium (coating) and titanium (TiP) and a calcium over phosphate ratio of 1.4-1.5 and a calcium over silicium ratio of 1.3-1.4 (FIG. 4). Coated TiP were subjected to X ray sterilization. Uncoated TiP were sterilized in an autoclave.

Impaction of allografts and titanium granules was standardized by dropping a weight of 9.8 g thirty times from a height of 33 cm along a sliding thread (Ø 2.0 mm, 9.8 g) which acts as an impactor to mimic manual impaction. Five specimens of every graft group, including five non impacted specimens of BoP, were not implanted but used for quantification of degree of impaction: specimens of BoP were prepared in stiff plastic tubes with an inner diameter of 2.0 mm, non implanted TiP specimens were prepared in BCC's. Cross sectional mineralized bone matrix area was determined from undecalcified central longitudinal slices (20 μm, Leica SP1600 saw-microtome, Leica Instruments GmbH, Nussloch, Germany) by light microscopy (Goldner staining). Cross sectional titanium area was determined by BEI from longitudinal cutted specimens after wet surface polishing (grid 200, 400, 800, 1200, 2400). Bone volume fraction and titanium volume fraction were calculated with interactive computer controlled image analysis by dividing the mineralized bone matrix area respectively titanium area by the whole graft cylinder area. After impaction specimens were stored frozen (−40° C.) under sterile conditions and thawn before implantation. The mean distance between implanted chambers was 14 mm (12-19 mm).

Twelve Dutch milk goats (Capra Hircus Sanus) with a mean weight of 47 kg (38-59 kg) were operated after approval of the ethical committee on animal experiments. Animals were housed together in a climatologically controlled room at least one week prior to surgery (tenderfood bottom, 18-22° C., humidity 60%) and provided with fresh hay, concentrate, pulp and water. The goats were anesthetized with pentobarbital (1200 mg) and isoflurane. A longitudinal incision was used to expose bilaterally the proximal medial metaphysis of the tibia. After local excision of periosteum (biopsy punch Ø 6.0 mm, Stiefel Laboratorium GmbH, Offenbach am Main, Germany) a drilling and tapping guide block was fixated with k-wires. A measuring device was used for standardizing the distance between the mal and the anteromedial tibial plateau. Six BCC's were screwed into position in every tibia till the hexagonal cap made firm contact with the cortex. For closure of superficial fascia and skin a 2.0 monofilament suture was used. After the implantation procedure animals received subcutaneous ampicillin (Albipen LA, Intervet International BV, Boxmeer, The Netherlands) (15 mg/kg/48 h) three times. Pain medication consisted of flunixine (75 mg/24 h) three times and buprenorfine (0.3 mg/12 h) twice.

Fluorochromes were administered during three subsequent days at four weeks (tetracycline), eight weeks (calcein green) and twelve weeks (alizarine) after operation to observe time dependence of bone apposition. Goats were killed one day after administration of the last doses of alizarine with an overdose pentobarbital (2.4 g). BCC's with surrounding cortex were fixed in 4% buffered formalin. After three days the content was fixated additionally. Serial slices of 40 µm parallel to the longitudinal axis of the chamber were made of which three sections were used for histologic quantification: one central section and two peripheral sections (300 µm from the centre of the specimen).

Fluorescence was classified subjectively by one person (LW) on an increasing 0-3 scale; 0: no fluorescence, 1: little fluorescence, some narrow bands, 2: clear fluorescence, intermediate apposition bands, 3: abundant fluorescence with broad apposition bands. Quantification of maximum bone ingrowth distance was done by another person (LD) by light microscopy (Goldner staining) and interactive computer controlled image analysis. Maximum bone ingrowth distance was defined as the largest distance between the bottom of the bone chamber and new bone in the graft cylinder, measured parallel to the longitudinal axis of the slice.

Univariate analysis of variance was performed with the factors goat, implant position and graft group to analyze differences between groups in fluorochrome score and differences between groups in maximum bone ingrowth distance. Normality and homogenity of variance were tested using Kolmogorov-Smirnov's and Levene's test. Post-hoc t-tests (Tukey) were used to determine differences between groups. Statistical analysis was performed with SPSS 9.0 (SPSS Inc., Chicago, United States).

The titanium volume fraction of individual TiP was 26±4%. Graft cylinders of unimpacted TiP (11-14 individual particles) showed a slightly lower titanium volume fraction. Impacted specimens consisted of 25-30 particles and showed a corresponding increase in titanium volume fraction. Titanium particles were slightly smaller than bone particles. About 15-18 bone chips could be impacted in the BCC which resulted in graft cylinders with a bone volume fraction of 61±9%. Impacted graft cylinders of both TiP and BoP were very dense. Longitudinal cross-sections of impacted TiP graft cylinders showed that only very small pores (10-50 µm) were visible in the center of TiP graft. Somewhat larger pores (50-75 µm) and openings between the TiP and the inner surface of the BCC could be found at the periphery (FIG. 17).

All implantations were uneventful. One goat died five days after operation from sepsis from an intestinal clostridium infection. One of the goats suffered from a unilateral superficial wound infection which healed uneventful. Post-mortem X-rays twelve weeks after implantation showed cortical thickening and unchanged implant positions without any signs of fracture or osteolysis, corresponding to good fixation and no signs of infection as observed during harvesting of the BCC's.

Six graft cylinders were damaged during histological preparation and therefore not available for histologic analysis (B: Two specimens, E: four specimens).

Fluorescence scores were highest in groups B and E during the whole implantation period. After four weeks only little bone apposition was found in all graft groups (no significant differences in tetracyclin score). Most fluorochrome activity was seen four weeks later with significantly higher calcein scores in group B and E compared to groups Tc ($p<0.05$), Ti and Tci ($p<0.001$). At the end of implantation fluorochrome activity decreased. Alizarin score was significantly higher in groups B and E compared to groups T ($p<0.05$), Ti and Tci ($p<0.01$). Most bone ingrowth seemed to have incurred eight weeks after implantation. Between eight and twelve weeks there was a clear increase in bone apposition compared to the already observed bone quantity after eight weeks, but a smaller increase in bone ingrowth distance.

In groups E and B a small cap of fibrous tissue preceded the invading bone, creating a fibrous transformation zone in graft cylinders of impacted bone chips. Fibrous tissue penetrated the whole graft cylinder of TiP up to the cap of the bone chamber in all specimens. The bone ingrowth front was quite fluent and easy to determine in empty BCC's and impacted BoP. However, bone ingrowth into TiP appeared to take place mainly in the periphery of graft cylinders, with some spots of bone formation in the more central part of the graft cylinder, especially in graft cylinders of impacted TiP.

Maximum bone ingrowth distance was chosen instead of mean bone ingrowth distance like used previously in bone chamber studies. Maximum bone ingrowth distance after twelve weeks showed large variation within groups and was smaller in TiP than in impacted BoP or empty BCC's. Maximum bone ingrowth distance was highest in groups E and B: 3.6±2.0 mm respectively 2.0±1.0 mm, $p<0.001$ (Table 2). Bone ingrowth was significantly lower in all four groups of TiP compared to groups B (, $p<0.05$) and E (, $p<0.001$). Impacted TiP showed a trend towards smaller bone ingrowth distances in both coated and uncoated groups ($p=0.2$). Coated TiP did not seem to perform better than uncoated TiP ($p=0.3$). BEI/EDS did not show any signs of remnants of the Bonitmatrix® coating. Coated and non-coated TiP showed a comparable interface distribution in terms of presence/absence of direct contact between bone and titanium (FIG. 11).

Corresponding to the in-vivo invasion of bone grafts, in the BCC ingrowing bone is preceded by ingrowing fibrous tissue which, besides improving tensile strength properties, almost doubles the compressive strength of impacted grafts four weeks after implantation. Although fibrous armoring may be sufficient for the long term stabilization of a reconstruction made with non-resorbable materials, the ingrowth of new bone seems preferable.

The small quantity of bone ingrowth in unimpacted TiP can be a point of interest in this study as titanium is known to be osteoconductive and therefore TiP might be expected to even potentiate osteoconductivity of the BCC instead of impairing it.

Several possible explanations could be given to explain the rather small bone ingrowth distance in TiP. The porosity of individual TiP was almost equal to the porosity of non impacted TiP graft cylinders. This indicates that deformation of TiP took place during manual insertion into BCC's.

The heaping of TiP was more effective in the central part of the graft cylinder and less effective at the periphery where particles were in contact with the flat surrounding inner surface of the BCC. Although bone ingrowth was seen even into pores as small as 50 micrometer in TiP cylinders, a hypothesis of occlusion by impaction seems to be supported by the ingrowth pattern of bone which took mainly place at the periphery of TiP graft cylinders, especially in impacted specimens. Variation and range of ingrowth distances in TiP cylinders might indicate that in the presence of pores, TiP could demonstrate their osteoconductive potential.

As seen in in-vivo reconstructions, impaction process results in quite porous graft layers which allow for penetration of bone cement, and individual bone chips and their macropores can often still be recognized.

Slightly larger particles that still showed macropores were also completely compressed by the applied impaction procedure. Therefore the applied deformation might exceed clinical applied impaction. Over-impaction would not only jeopardize bone ingrowth in BoP but also osteoconduction of TiP.

Addition of a CaP coating seemed to compensate to some extent the impairing effect of impaction of bone ingrowth.

Bone in Growth in Ti Particles

In table 4 six groups of grafts are shown, which were used in filling similar defects in a goats femurcondyl, in cylindrical defects. The defects had a diameter of 8 mm and a height of 10 mm, leading to a volume of 0.5 ml. All grafts were impacted as defined before. Uncoated Ti particles had a density of 0.5 g/ml (density A) The mass per defect was increased in case of coated particles, in order to maintain the Ti density similar in all defects. The TiPc1 coating was formed by calcium phosphate (tricalcium phosphate and hydroxyapetite) It made out approximately 7 weight % of the total mass. The coating of TiPc2 was calcium phosphate (carbonated apatite) and formed approximately 11 weight % of the total mass.

TABLE 4

| groep | partikel diameter (mm) | grafts massa per defect (g) |
|---|---|---|
| BoP | 3-5 | 0.9 |
| CeP | 2-4 | 0.8 |
| TiP | 3-5 | 0.55 |
| TiP/BoP | 3-5 | 0.45/0.25 |
| TiPc1 | 3-5 | 0.59 |
| TiPc2 | 3-5 | 0.61 |

Figure 20A:
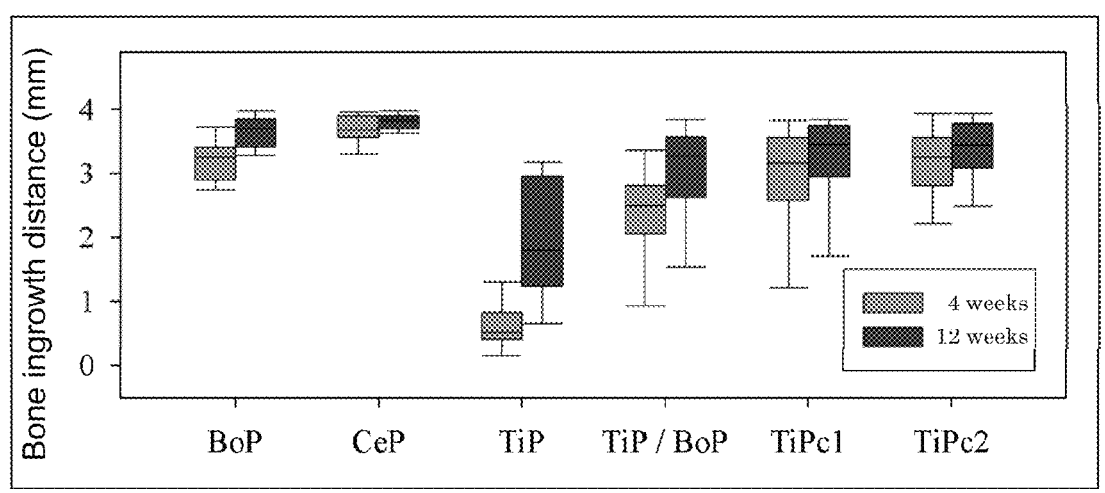

With each group 12 defects were filled in the femurcondyl of said goats, after which the in growth distance was defined after 4 and 12 weeks by sawing the bone across (perpendicular to the length direction) showing substantially circular cross sections of the filled defects. Each circle was divided into four quarts, and the in growth was defined in each quart as the radial distance of in growth, after which the average in growth was defined as the average of these four quarts. In FIG. 20 a cross section is shown with a circle 50 drawn in, indicating the outer periphery of the defect, and four quadrants 51, each showing an arrow 52 indicating the in growth distance. Titanium in the defect is shown in black, bone in grey. In FIG. 20A a diagram is shown in which for the groups of grafts defined in table 3 the average in growth is shown after 4 weeks and 12 weeks. This clearly shown that for these samples and defects the in growth distance for uncoated TiP is smallest after 4 weeks but comparable to said distance of the coated TiP grafts after 12 weeks and slightly smaller than in BoP and CeP.

Goat Tests

A large load bearing defect (segmental and cavitary) in the acetabulum of 10 goats was reconstructed with a wire mesh and with TiP.

One goat failed because of a femoral fracture not related to the acetabular reconstruction. In one goat a luxation of the cup was found but the Tip layer was intact. In one goat the cup was loose upon offering but again the TiP layer was intact. Macroscopically the cement had penetrated the layer of TiP. After 15 weeks fluorochrome labels showed abundant new bone formation had taken place in the layer of TiP of all goats. In some goats the new bone formation was found up to the interface with the cement layer. In most areas no soft tissue interface or a very thin soft tissue interface was present between the layer of TiP and the cement layer. The blood levels of Ti during the follow up period were low. In the thick sections no accumulations of Ti debris was present in any of the goats.

Large defect in the acetabulum of goats can be reconstructed with impacted TiP. The soft tissue interface is thinner than in similar previous experiments in the same model in which the same defect was reconstructed with MCB or a mixture of MCB with TCP/HA layer.

In the present study we reconstructed the same defect with impacted layer of titanium particles (TiP). The main questions addressed were the extent of bone ingrowths into the layer of TiP, the nature of the interface between TiP layer and the cement layer, the potential generation of small Ti particles in the reconstruction, and the Ti blood levels.

Materials and Methods

Animal Model

The study was performed on 10 adult female Dutch milk goats (*Capra Hircus* Sana). All animals were skeletally mature and weighed between 50 and 60 kg (mean 55 kg). The follow up period was 15 weeks.

Materials

Titanium Particles (porosity of 75-80% %, diameter of 2.8-4 mm) were provided by Fondel Finance BV (Rotterdam, the Netherlands). Al TiP particles were cleaned according to the protocols for clinical use by Cam Implants BV (Leiden, the Netherlands). All TiP were coated with a layer of calcium phosphate according to the method previously published by Kukubo (Yan W Q, Nakamura T, Kawanabe K, Nishigochi S, Oka M, Kokubo T. Apatite layer-coated titanium for use as bone bonding implants. Biomaterials 1997; 18:1185-1190). The coating has been applied by Biomaterialen, Radbout University, Nijmegen).

Surgical Procedure

Pre-operatively, an antibiotic injection (Baytril 0.2 ml/kg; Bayer, Division Animal Health, Mijdrecht, the Netherlands) was administered intramuscularly. Pre-operative pain management consisted of intramuscular administration of both buprenorphine hydrochloride (Temgesic 5 µg/kg; Renckitt Benkiser Healthcare, Hull, United Kingdom) and a non-steroidal anti-inflammatory drug, fluxin meglumine (Finadyne 1 mg/kg; Schering-Plough Animal Health, Brussels, Belgium). Intra-operatively, the pain suppression was maintained further by an intra-venous injection of sodiumpentobarbital (Nembutal 30 mg/kg; Ceva Sante Animale, Maassluis, the Netherlands). Surgery was performed with the animals lying on their left side using isoflurane anesthesia (2.5% isoflurane on a oxygen/nitro-oxygen mixture). The incision site was shaved and thoroughly cleaned with betadine. Thereafter, a C-shaped incision was used to approach the right hip from the anterior side. The gluteal muscles were partially loosened from the femur and retracted. The capsule was opened with a T-shaped incision and thereafter the femoral head was dislocated. Next, a femoral neck osteotomy was performed. The acetabulum was reamed up to a diameter of 32 mm and using a high speed power drill, the superolateral rim was removed to simulate a segmental defect as observed frequently in hip revision surgery. The resulting type 3 AAOS segmental defect was reconstructed with a metal mesh (X-Change metal mesh, Stryker Orthopedics, Newbury, United Kingdom) which was secured to the outer side of the pelvic bone with four AO bone screws (diameter 3.5 mm; length of 10 or 20 mm; Synthes, Switzerland). Small burr holes (2 mm) were made in the dense bone areas of the acetabulum wall to facilitate vascularization of the bone graft. After a trial testing of the cup, the defect was reconstructed with TiP. Ca. 5-11 grams of TiP was used for each reconstruction. Several dome shaped impactors varying in size from 26 mm to 32 mm and comparable to the Acetabular X-change® revision set (Stryker Orthopedics, Newbury, United Kingdom) were used for impaction. The inner diameter of the reconstructed defect was 32 mm in diameter. Next, bone cement (Surgical Simplex-P, Stryker Orthopedics, Newbury, United Kingdom) was introduced into the defect 4 minutes after mixing the powder with the monomer and thereafter pressurized for two minutes. A custom made Exeter sheep polyethylene cup (inner diameter 22.2 mm, outer diameter 29 mm) was inserted 6 minutes after mixing. Next, the femoral shaft was opened and cleared with broaches. The femoral canal was ravaged and bone cement was injected retrograde 3.5 minutes after mixing the bone cement components. A double-tapered polished V40 Exeter sheep stem (Stryker, Benoist Girard, France) was inserted 5 minutes after mixing the bone cement. After setting of the cement, the hip was reduced. The soft tissues were closed in layers and a control X-ray was made of the hip region. Postoperatively, the animals were placed in a hammock for ca 10 to 14 days. They received ampicilline antibiotics (Albipen LA 15 mg/kg; Intervet, Boxmeer, the Netherlands) for another 48 hours and also intramuscular injections of Finadyne (4 days) and Temgesic (2 days) for pain suppression. Afterwards, the goats were housed in an out door farm with ample space to walk around. Each goat received a subcutaneous injection of calcein green solution (25 mg/kg) at 8 and 1 days before killing to allow histological assessment of bone formation at the time of offering.

The goats received fluorochromes during the follow up period (Tetracycline, calcein green and xylenol orange) and they were killed at 15 weeks postoperatively, with an overdose of barbiturate (Nembutal 60 mg/kg). Standard roentgen photographs were taken from the implant sites to verify the implant position and to exclude fractures and dislocations. Both the femur and the reconstructed acetabulum were harvested, cleaned from all soft tissue and fixed in a 4% buffered formaldehyde solution at 4° C. for at least ten days.

Histology

After making contact X-ray photos of the retrieved hip components, the reconstructed acetabular defects were macroscopically dissected into several parts according to the two halves. All parts were dehydrated and embedded non-decalcified in polymethylmethacrylate (PMMA) and serial sectioned at a Leica SP1600 saw-microtome, Heidelberg, Germany, sections circa 50 microns thickness). Sections were inspected non-stained. After quantification of bone ingrowth they were HE-stained or left unstained for the visualization of calcein fluorescence. All sections were observed under ordinary and fluorescent light.

In one section of every specimen the thickness of the interface was measured at five locations at equal distance from each other. To determine the location where measurements were carried out a tangent was drawn along the acetabulum. From the center of the cup five lines at equal corners (30 degrees) were drawn and at the intersections with the soft tissue interface measurements were carried out. All values of one goat were averaged.

Clinical Observations and Complications.

One goat broke his femur, which was a complication after surgery and which was probably not directly related to the reconstructive surgery. During the first two weeks after release from the hammock all goats limped, but thereafter it improved to almost normal walking in all animals. One cup was completely loose upon offering and one cup was slightly loose.

Histological Analysis.

Based on the thick sections (FIG. 21-23). In all specimens the layer of TiP had been integrated into the host bone (FIG. 24). Bone was intimately connected to the outer layer of the TiP layer (FIG. 22). In all specimens a considerable ingrowth of new bone was found in the larger voids in-between individual TiP granules (FIG. 23).

Fibrous Tissue Formation.

In most specimens new bone had reached the TiP cement interface (FIG. 23). The interface between TiP and cement was rather tight and in most cases a direct connection was found between TiP layer and cement (FIG. 23). In some locations a relatively thin fibrous tissue interface was found that was in general thinner then 100 microns (FIG. 23). This is substantially smaller than was expected and smaller than when using bone graft.

Ti Levels in Blood.

Preoperative TiP ion levels were ca 0.6 PPB. During the follow up period this level slowly increased to ca 1.0 PPB (FIG. 25), which was surprisingly low.

In previous publications on the model used to test TCP/HA MCB mixture, the main complication was a fracture of the acetabular wall. The fracture of the medial wall is related to the goat model. After reaming with a 32 mm reamer to create a reproducible cavitary defect, especially in some goats with smaller bone dimensions, the medial wall is extremely thin. During the impaction process with TCP/HA the thin medial wall is fractured in these cases. In this series no perforation of the medial wall was observe. This can be related to the impactability of TiP, which can lead to a more homogeneous distribution of stresses over the medial wall bone.

A second observation in this model was that in all three studies performed previously a relatively thick interface developed between the incorporated bone graft and the cement layer (Arts J J, Gardeniers J W, Welten M L, Verdonschot N, Schreurs B W, Buma P. No negative effects of bone impaction grafting with bone and ceramic mixtures. Clin Orthop 2005; 438:239-247; Buma P, Arts J J, Gardeniers J W, Verdonschot N, Schreurs B W. No effect of bone morphogenetic protein-7 (OP-1) on the incorporation of impacted bone grafts in a realistic acetabular model. J Biomed Mater Res B Appl Biomater 2007; Schimmel J W, Buma P, Versleyen D, Huiskes R, Slooff T J. Acetabular reconstruction with impacted morselized cancellous allografts in cemented hip arthroplasty: a histological and biomechanical study on the goat. J Arthroplasty 1998; 13:438-448). In contrast, in this study no or only a very thin layer of fibrous tissue is present between the TiP layer and cement. Probably the soft tissue interface is formed in the process in which the MCB is desorbed. Potentially this leads to a weakening of the remodelling graft layer and cement. In case of TiP layer the integrity of the TiP cement layer can be strengthened by the ingrowth of bone. No weakening by remodelling shall occur which might explain the very favourable results with respect to interface development.

Finally Ti levels were lower then in clinical series in which ti non-cemented implants were used (FIG. 25).

In conclusion, the results of this animal experiment are favourable. Bone ingrowths in all reconstructions were found. Even in goats in which the cup had been luxated or was loose, an intact layer of TiP was found.

The present invention is by no means limited to the embodiments shown and described. Many variations are possible within the scope of protection claimed by the claims. It should especially be noted that the method or a kit of parts according to the invention can be used in other parts of the human or animal body, for example for different prosthesis. TiP may be mixed with for example BoP and/or CeP but preferably only TiP are used. A prosthesis if applicable can have any desired shape and size. These alternatives are also considered to be covered by the scope of the appending claims.

The invention claimed is:

1. Kit of separate parts comprising
a prosthesis or prosthesis part having at least one contact surface;
metal granules having an internal porosity; and
bone cement,
wherein the bone cement, the metal granules and the prosthesis or prosthesis part are individually inserted within a patient's body,
wherein the granules cover the at least one contact surface with a layer of granules having an average thickness of at least one time the average size of the granules,
wherein the bone cement covers the layer of granules while the layer of granules are covering said at least one contact surface, and the bone cement penetrates the layer of granules over a distance of at least 2 mm.

2. Kit of parts according to claim 1, further comprising a mesh material for covering at least part of an outer surface formed by a layer of said granules on said at least one contact surface.

3. Kit of parts according to claim 2, wherein said mesh is such that said granules can be contained by said mesh.

4. Kit of parts according to claim 1, further comprising means for compacting said granules in an opening in a bone.

5. Kit of parts according to claim 4, wherein said compacting means is provided with a contact part having a configuration similar to at least one contact surface to be introduced into said opening.

6. Kit of parts according to claim 1, further comprising means for introducing said granules into an opening in a bone.

7. Kit of parts according to claim 1, wherein at least 50% of said granules by volume has an average size between 1 and 10 mm.

8. Kit of parts according to claim 7, wherein substantially all of said granules have an average size between 1 and 10 mm.

9. Kit of parts according to claim 1, wherein said granules have an average porosity of 40-90%.

10. Kit of parts according to claim 1, wherein said granules have a surface roughness over 5.5 Ra.

11. Kit of parts according to claim 1, wherein said granules have been formed using a method of purification of titanium with titanium tetrachloride ($TiCl_4$).

12. Kit of parts according to claim 1, wherein said granules have an osteoconductive coating of calcium phosphate or bioactive glass.

13. Kit of parts according to claim 12, wherein said coating has an average thickness of 0.5 to 100 micrometer.

14. Kit of parts according to claim 1, wherein said granules are made at least partly of titanium.

15. Kit of parts according to claim 1, wherein said bone cement includes an acrylate.

16. Titanium granules for use in a kit of parts according to claim 1, having between 50 and 95% porosity and a diameter between 1 and 10 mm, which granules are osteoconductive, which granules are coated with osteoconductive or osteoinductive coatings, or coatings comprising bioceramic, bioglass or osteoconductive or osteoinductive molecules or fluids or cells.

17. Kit of parts, according to claim 1, further comprising a compacting device wherein said compacting device has a longitudinal direction and is provided with an impact surface at a longitudinal end for driving said compacting device in said longitudinal direction, and an at least partly tapering portion, tapering in a direction facing away from said impact surface.

18. Kit of parts according to claim 1, wherein the amount of granules is sufficient to cover the at least one contact surface with a layer of granules having an average thickness of between 1 and 10 times the average size of the granules.

19. Kit of parts according to claim 1, wherein the amount of granules is sufficient to cover the at least one contact surface with a layer of granules having an average thickness of between 1 and 4 times the average size of the granules.

20. Kit of parts according to claim 1, wherein the amount of bone cement is sufficient to cover the granules in a layer of granules covering said at least one contact surface to a depth of at least 2 mm plus a penetration distance into the layer of granules over an average distance of 2-X mm, wherein X is equal to the diameter of a granule in an upper size range in said layer of granules.

21. Kit of separate parts comprising
a prosthesis or prosthesis part having at least one contact surface;
metal granules having an internal porosity; and
bone cement,
wherein the bone cement, the metal granules and the prosthesis or prosthesis part are individually inserted within a patient's body,
wherein the granules cover the at least one contact surface with a layer of granules having an average thickness of at least one time the average size of the granules, and
wherein the cement fills pores of said granules and openings between said granules up to an average of at least one third of said layer of granules.

22. Kit of parts according to claim 21, wherein the amount of granules is sufficient to cover the at least one contact surface with a layer of granules having an average thickness of between 1 and 10 times the average size of the granules.

23. Kit of parts according to claim 21, wherein the amount of granules is sufficient to cover the at least one contact surface with a layer of granules having an average thickness of between 1 and 4 times the average size of the granules.

24. Kit of parts according to claim 21, further comprising a mesh material for covering at least part of an outer surface formed by a layer of said granules on said at least one contact surface.

25. Kit of parts according to claim 24, wherein said mesh is such that said granules can be contained by said mesh.

26. Kit of parts according to claim 21, further comprising means for compacting said granules in an opening in a bone.

27. Kit of parts according to claim 26, wherein said compacting means is provided with a contact part having a configuration similar to at least one contact surface to be introduced into said opening.

28. Kit of parts according to claim 21, further comprising means for introducing said granules into an opening in a bone.

29. Kit of parts according to claim 21, wherein at least 50% of said granules by volume has an average size between 1 and 10 mm.

30. Kit of parts according to claim 29, wherein substantially all of said granules have an average size between 1 and 10 mm.

31. Kit of parts according to claim 21, wherein said granules have an average porosity of 40-90%.

32. Kit of parts according to claim 21, wherein said granules have a surface roughness over 5.5 Ra.

33. Kit of parts according to claim 21, wherein said granules have been formed using a method of purification of titanium with titanium tetrachloride ($TiCl_4$).

34. Kit of parts according to claim 21, wherein said granules have an osteoconductive coating of calcium phosphate or bioactive glass.

35. Kit of parts according to claim 34, wherein said coating has an average thickness of 0.5 to 100 micrometer.

36. Kit of parts according to claim 21, wherein said granules are made at least partly of titanium.

37. Kit of parts according to claim 21, wherein said bone cement includes an acrylate.

38. Titanium granules for use in a kit of parts according to claim 1, having between 50 and 95% porosity and a diameter between 1 and 10 mm, which granules are osteoconductive, which granules are coated with a coating of osteoconductive or osteoinductive coatings, or coatings comprising bioceramic, bioglass or osteoconductive or osteoinductive molecules or fluids or cells.

39. Kit of parts, according to claim 21, further comprising a compacting device wherein said compacting device has a longitudinal direction and is provided with an impact surface at a longitudinal end for driving said compacting device in said longitudinal direction, and an at least partly tapering portion, tapering in a direction facing away from said impact surface.

40. Kit of separate parts comprising
a prosthesis or prosthesis part having at least one contact surface;
metal granules having an internal porosity; and
bone cement,
wherein the kit of parts is arranged such that during use, when the bone cement, the metal granules and the prosthesis or prosthesis part are inserted into a patient's body,
the granules cover the at least one contact surface with a layer of granules having an average thickness of at least one time the average size of the granules,
wherein the bone cement covers the layer of granules while the layer of granules are covering said at least one contact surface, and the bone cement penetrates the layer of granules over a distance of at least 2 mm.

41. Kit of parts according to claim 40, wherein the amount of granules is sufficient to cover the at least one contact surface with a layer of granules having an average thickness of between 1 and 10 times the average size of the granules.

42. Kit of parts according to claim 40, wherein the amount of granules is sufficient to cover the at least one contact surface with a layer of granules having an average thickness of between 1 and 4 times the average size of the granules.

43. Kit of parts according to claim 40, further comprising a mesh material for covering at least part of an outer surface formed by a layer of said granules on said at least one contact surface.

44. Kit of parts according to claim 43, wherein said mesh is such that said granules can be contained by said mesh.

45. Kit of parts according to claim 40, further comprising means for compacting said granules in an opening in a bone.

46. Kit of parts according to claim 45, wherein said compacting means is provided with a contact part having a configuration similar to at least one contact surface to be introduced into said opening.

47. Kit of parts according to claim 40, further comprising means for introducing said granules into an opening in a bone.

48. Kit of parts according to claim 40, wherein at least 50% of said granules by volume has an average size between 1 and 10 mm.

49. Kit of parts according to claim 48, wherein substantially all of said granules have an average size between 1 and 10 mm.

50. Kit of parts according to claim 40, wherein said granules have an average porosity of 40-90%.

51. Kit of parts according to claim 40, wherein said granules have a surface roughness over 5.5 Ra.

52. Kit of parts according to claim 40, wherein said granules have been formed using a method of purification of titanium with titanium tetrachloride ($TiCl_4$).

53. Kit of parts according to claim 40, wherein said granules have an osteoconductive coating of calcium phosphate or bioactive glass.

54. Kit of parts according to claim 53, wherein said coating has an average thickness of 0.5 to 100 micrometer.

55. Kit of parts according to claim 40, wherein said granules are made at least partly of titanium.

56. Kit of parts according to claim 40, wherein said bone cement includes an acrylate.

57. Titanium granules for use in a kit of parts according to claim 40, having between 50 and 95% porosity and a diameter between 1 and 10 mm, which granules are osteoconductive, which granules are coated with a coating of osteoconductive or osteoinductive coatings, or coatings comprising bioceramic, bioglass or osteoconductive or osteoinductive molecules or fluids or cells.

58. Kit of parts, according to claim 40, further comprising a compacting device wherein said compacting device has a longitudinal direction and is provided with an impact surface at a longitudinal end for driving said compacting device in said longitudinal direction, and an at least partly tapering portion, tapering in a direction facing away from said impact surface.

59. Kit of separate parts comprising
a prosthesis or prosthesis part having at least one contact surface;
metal granules having an internal porosity; and
bone cement,
wherein the kit of parts is arranged such that during use, when the bone cement, the metal granules and the prosthesis or prosthesis part are inserted into a patient's body,
the granules cover the at least one contact surface with a layer of granules having an average thickness of at least one time the average size of the granules, and
wherein the cement fills pores of said granules and openings between said granules up to an average of at least one third of said layer of granules.

60. Kit of parts according to claim 59, wherein the amount of granules is sufficient to cover the at least one contact surface with a layer of granules having an average thickness of between 1 and 10 times the average size of the granules.

61. Kit of parts according to claim 59, wherein the amount of granules is sufficient to cover the at least one contact surface with a layer of granules having an average thickness of between 1 and 4 times the average size of the granules.

62. Kit of parts according to claim 59, further comprising a mesh material for covering at least part of an outer surface formed by a layer of said granules on said at least one contact surface.

63. Kit of parts according to claim 62, wherein said mesh is such that said granules can be contained by said mesh.

64. Kit of parts according to claim 59, further comprising means for compacting said granules in an opening in a bone.

65. Kit of parts according to claim 64, wherein said compacting means is provided with a contact part having a configuration similar to at least one contact surface to be introduced into said opening.

66. Kit of parts according to claim 59, further comprising means for introducing said granules into an opening in a bone.

67. Kit of parts according to claim 59, wherein at least 50% of said granules by volume has an average size between 1 and 10 mm.

68. Kit of parts according to claim 67, wherein substantially all of said granules have an average size between 1 and 10 mm.

69. Kit of parts according to claim 59, wherein said granules have an average porosity of 40-90%.

70. Kit of parts according to claim 59, wherein said granules have a surface roughness over 5.5 Ra.

71. Kit of parts according to claim 59, wherein said granules have been formed using a method of purification of titanium with titanium tetrachloride ($TiCl_4$).

72. Kit of parts according to claim 59, wherein said granules have an osteoconductive coating of calcium phosphate or bioactive glass.

73. Kit of parts according to claim 72, wherein said coating has an average thickness of 0.5 to 100 micrometer.

74. Kit of parts according to claim 59, wherein said granules are made at least partly of titanium.

75. Kit of parts according to claim 59, wherein said bone cement includes an acrylate.

76. Titanium granules for use in a kit of parts according to claim 59, having between 50 and 95% porosity and a diameter between 1 and 10 mm, which granules are osteoconductive, which granules are coated with a coating of osteoconductive or osteoinductive coatings, or coatings comprising bioceramic, bioglass or osteoconductive or osteoinductive molecules or fluids or cells.

77. Kit of parts, according to claim 59, further comprising a compacting device wherein said compacting device has a longitudinal direction and is provided with an impact surface at a longitudinal end for driving said compacting device in said longitudinal direction, and an at least partly tapering portion, tapering in a direction facing away from said impact surface.

* * * * *